(12) United States Patent
Chen et al.

(10) Patent No.: US 6,251,906 B1
(45) Date of Patent: Jun. 26, 2001

(54) RETROVIRAL PROTEASE INHIBITING COMPOUNDS

(75) Inventors: Xiaoqi Chen, San Mateo, CA (US); Dale J. Kempf, Libertyville, IL (US); Daniel W. Norbeck, Grayslake, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/309,141

(22) Filed: May 10, 1999

Related U.S. Application Data

(60) Provisional application No. 60/085,709, filed on May 15, 1998.

(51) Int. Cl.[7] ............... A61K 31/495; A61K 31/50; C07D 47/00; C07D 405/00
(52) U.S. Cl. ............... 514/254.02; 514/254.11; 514/249; 544/367; 544/377; 544/349
(58) Field of Search .................. 514/249, 254.11, 514/254.02; 544/349, 377, 367

(56) References Cited

U.S. PATENT DOCUMENTS

| 5,157,041 | 10/1992 | Handa et al. | 514/314 |
|---|---|---|---|
| 5,455,351 | 10/1995 | Kempf et al. | 44/366 |
| 5,541,206 | 7/1996 | Kempf et al. | 514/365 |

FOREIGN PATENT DOCUMENTS

| 0486948 | 5/1992 | (EP). |
|---|---|---|
| 0560268 | 3/1993 | (EP). |
| 0560269 | 3/1993 | (EP). |
| 0541168 | 5/1993 | (EP). |
| 9405639 | 3/1994 | (WO). |
| 9414436 | 7/1994 | (WO). |
| 9516688 | 6/1995 | (WO). |
| 9740029 | 10/1997 | (WO). |

OTHER PUBLICATIONS

Dorsey et al."The Design of a Pot.& Orally Biov. HIV Prot.Inhibi."J.Med.Chem. '94,37/21,3443–51, Apr. 1994.*
Getman et al."Disc.of a Novel class of Potent HIV–1 Prot.Inhi.Cont." J.Med.Chem.'93,36,288–91, Apr. 1994.*
Dorsey et al. L–735,524: The Design of a Potent and Orally Bioavailable HIV Protease Inhibitor Journal of Med Chem.1994 vol. 37 No. 21 pg. 3443–3451.
Getman et al. Discovery of a Novel Class of Potent HIV–1 Protease Inhibitors Containing the (R)–(Hydrosyethyl)Urea Isostere J. Med. Chem. 1993 36, 288–191.
Kempf, et al., Journal of Medicinal Chemistry 41 602–617 (1998).
Chen, et al., Bioorganic & Medicinal Chemistry Letters 8 3531–3536 (1998).

* cited by examiner

*Primary Examiner*—Mukund J. Shah
*Assistant Examiner*—Sudhaker B. Patel
(74) *Attorney, Agent, or Firm*—Steven R. Crowley

(57) ABSTRACT

The present invention discloses novel compounds, compositions, and methods for inhibiting retroviral proteases and in particular for inhibiting human immunodeficiency virus (HIV) protease. The present invention also relates to compositions and methods for treating a retroviral infection and in particular an HIV infection, and to processes for making such compounds and synthetic intermediates employed in these processes.

30 Claims, No Drawings

RETROVIRAL PROTEASE INHIBITING COMPOUNDS

This application claims the benefit of U.S Provisional Application for Patent No. 60/085,709, filed May 15, 1998.

TECHNICAL FIELD

The present invention relates to novel compounds compositions and methods for inhibiting retroviral proteases and in particular for inhibiting human immunodeficiency virus (HIV) protease. The present invention also relates to compositions and methods for treating a retroviral infection and in particular an HIV infection, and to processes for making such compounds and synthetic intermediates employed in these processes.

BACKGROUND OF THE INVENTION

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease will provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 981 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS involve administration of compounds such as 3'-azido-3'-deoxythymidine (AZT), 2',3'-dideoxycytidine (DDC) and 2',3'-dideoxyinosine (DDI) and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

Recently the HIV protease inhibitors ritonavir, saquinavir, nelfinavir, and indinavir have been approved in the U.S. for treatment of HIV infections. However, there is a continuing need for improved HIV protease inhibitors.

SUMMARY OF THE INVENTION

The present invention comprises retroviral protease inhibiting compounds having formula I:

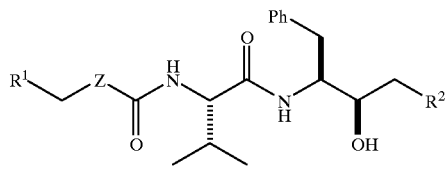

wherein $R^1$ is a thiazolyl group having the formula

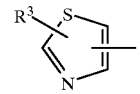

and $R^2$ is a group having the formula:

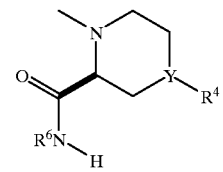

wherein $R^4$ group is $-WR^5$.

The $R^3$ group is selected from the group consisting of hydrogen, alkyl, amino, alkylamino, dialkylamino and cycloalkyl, and Y is CH or N. W is selected from the group consisting of —O—, —S—, or —(CH$_2$)$_n$—, where n is from 0 to 6, with the proviso that when W is O, or S then Y is CH. $R^5$ is selected from the group consisting of alkyl, and aryl. Optionally, $R^4$ and the ring to which it is attached, taken together can form a bicyclic group having the formula:

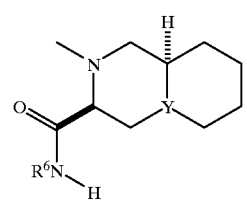

The $R^6$ group is hydrogen, alkyl, cycloalkyl, aryl, (aryl)alkyl, heterocyclic, (heterocyclic)alkyl, heteroaryl, or (heteroaryl)alkyl, Z is —O—, —S—, —CH$_2$— or —N($R^7$)—; and $R^7$ is hydrogen, alkyl, aryl, (aryl)alkyl, heterocyclic, (heterocyclic)alkyl, heteroaryl, or (heteroaryl)alkyl.

The present invention also comprises retroviral protease inhibiting compounds having formula II:

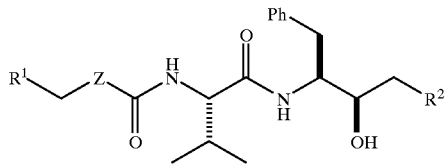

wherein R¹ is a thiazolyl group having the formula

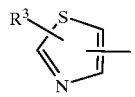

and R² is a group having the formula:

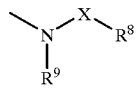

wherein X is —C(O)— or —S(O)₂— and R⁸ is alkyl, aryl, (aryl)alkyl, alkylamino, dialkylamino, heterocyclic, (heterocyclic)alkyl, heteroaryl, or (heteroaryl)alkyl.

R³ is selected from the group consisting of hydrogen, alkyl, amino, alkylamino, dialkylamino and cycloalkyl and R⁹ is alkyl, cycloalkyl, aryl, (aryl)alkyl, heterocyclic, (heterocyclic)alkyl, heteroaryl, or (heteroaryl)alkyl. The Z group is —O—, —S—, —CH₂— or —N(R⁷)—, and R⁷ is hydrogen, alkyl, aryl, (aryl)alkyl, heterocyclic, (heterocyclic)alkyl, heteroaryl, or (heteroaryl)alkyl.

The alkyl, aryl, heterocyclic, and heteroaryl groups in the compounds of the invention can be optionally substituted with from 1 to 5 substituents and preferrably from 1 to 3 substituents. The substituents are selected from the group consisting of hydroxy, alkoxy, alkylthio, amino, alkylamino, dialkylamino and halogen. The invention also includes pharmaceutically acceptable salts, esters or prodrugs of compounds I and II.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The present invention comprises retroviral protease inhibiting compounds having formula I:

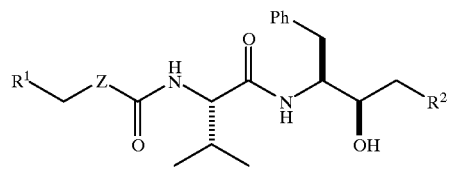

wherein R¹ is a thiazolyl group having the formula

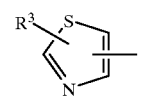

and R² is a group having the formula:

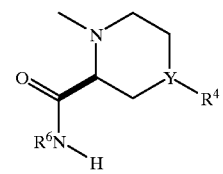

wherein R⁴ group is —WR⁵.

The R³ group is selected from the group consisting of hydrogen, alkyl, amino, alkylamino, dialkylamino and cycloalkyl, and Y is CH or N. W is selected from the group consisting of —O—, —S—, or —(CH₂)ₙ—, where n is from 0 to 6, with the proviso that when W is O, or S then Y is CH. R⁵ is selected from the group consisting of alkyl, and aryl. Optionally, R⁴ and the ring to which it is attached, taken together can form a bicyclic group having the formula:

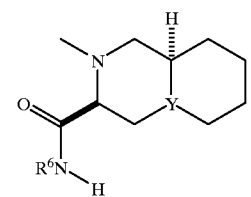

with the proviso that when W is O, or S then Y is CH. The R⁶ group is hydrogen, alkyl, cycloalkyl, aryl, (aryl)alkyl, heterocyclic, (heterocyclic)alkyl, heteroaryl,or (heteroaryl) alkyl, Z is —O—, —S—, —CH₂— or —N(R⁷)—; and R⁷ is hydrogen, alkyl, aryl, (aryl)alkyl, heterocyclic, (heterocyclic)alkyl, heteroaryl, or (heteroaryl)alkyl.

The present invention also comprises retroviral protease inhibiting compounds having formula II:

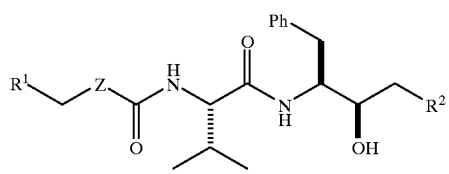

wherein R¹ is a thiazolyl group having the formula:

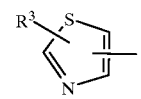

and $R^2$ is a group having the formula:

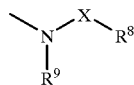

wherein X is —C(O)— or —S(O)$_2$— and $R^8$ is alkyl, aryl, (aryl)alkyl, alkylamino, dialkylamino, heterocyclic, (heterocyclic)alkyl, heteroaryl, or (heteroaryl)alkyl.

$R^3$ is selected from the group consisting of hydrogen, alkyl, amino, alkylamino, dialkylamino and cycloalkyl and $R^9$ is alkyl, cycloalkyl, aryl, (aryl)alkyl, heterocyclic, heteroaryl, or (heteroaryl)alkyl. The Z group is —O—, —S—, —CH$_2$— or —N($R^7$)—, and $R^7$ is hydrogen, alkyl, aryl, (aryl)alkyl, heterocyclic, (heterocyclic)alkyl, heteroaryl, or (heteroaryl)alkyl.

The alkyl, aryl, heteroaryl, and heterocyclic groups of the compounds of the invention, having formula I or II, can optionally be substituted with from 1 to 5 substituents and preferrably from 1 to 3 substituents. The substituents are selected from the group consisting of hydroxy, alkoxy, alkylthio, amino, alkylamino, dialkylamino and halogen. The invention also includes pharmaceutically acceptable salts, esters or prodrugs of compounds I and II.

In the compounds of the invention, a preferred $R^3$ group is alkyl or cycloalkyl. More preferred are compounds where $R^3$ is alkyl selected from the group consisting of methyl, ethyl, or propyl or cycloalkyl selected from the group consisting of cyclopropyl, cyclobutyl, cyclopentyl, and cyclohexyl. The most preferred $R^3$ group is isopropyl.

The preferred Z groups are —O—, or —N($R^7$)—. When Z is —N($R^7$)— a preferred $R^7$ is methyl.

In compounds having formula I, and $R^2$ is a group having the formula:

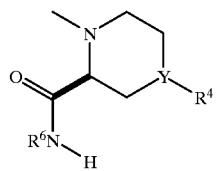

wherein Y is CH or N and $R^4$ is —W—$R^5$, the preferred $R^5$ group is aryl selected from the group consisting of phenyl, methylenedioxyphenyl, and heteroaryl. In compounds where Y is nitrogen, W is —(CH$_2$)$_n$—, $R^5$ is alkyl or aryl and n is from 0 to 6.

In compounds where Y is CH, a preferred W is —O—, and preferably, $R^5$ is alkyl, or aryl selected from the group consisting of phenyl, methylenedioxyphenyl, and heteroaryl.

The alkyl, aryl, heterocyclic, and heteroaryl groups can be substituted with from 1 to 5 substituents and preferrably from 1 to 3 substituents.

Examples of substituents, for the alkyl, aryl, heterocyclic, and heteroaryl groups, are selected from the group consisting of hydroxy, alkoxy, alkylthio, amino, alkylamino, dialkylamino and halogen. Preferred substituents are fluorine, hydroxy, alkoxy, or alkylthio groups. The preferred alkoxy is methoxy. The preferred halogen is fluorine.

In a preferred embodiment the alkyl or aryl groups can be substituted with one to three groups. The preferred substituents are hydroxy, methoxy or fluorine. The preferred aryl groups include phenyl, such as, for example, methylenedioxyphenyl, and heteroaryl such as, for example, furanyl, thienyl, benzothienyl, thiazolyl and the like. A preferred heteroaryl group is thiazolyl. In a preferred compound n is zero, and $R^5$ is methyl substituted with a thiazolyl group.

The $R^6$ group is selected from the group consisting of alkyl, hydroxyalkyl, and cycloalkyl. Preferably $R^6$ is lower alkyl group such as, for example, methyl, ethyl, propyl, butyl and the like. A preferred $R^6$ group is tert-butyl or hydroxy-butyl.

The $R^8$ group is selected from the group consisting of alkyl, aryl, (aryl)alkyl, alkylamino, dialkylamino, heterocyclic, (heterocyclic)alkyl, heteroaryl, or (heteroaryl)alkyl. A preferred $R^8$ group is (alkyl)amino, such as, for example, (tertbutyl)amino.

The preferred $R^9$ group is a lower alkyl group such as, for example propyl, butyl, pentyl and the like. More preferred $R^9$ groups are isopropyl, tert-butyl, isobutyl, 3-methyl-1-butyl, and the like. Most preferred is the iso-butyl group.

In a preferred compound of the invention X is —S(O)$_2$—, $R^8$ is aryl selected from the group consisting of phenyl, and heteroaryl and $R^9$ is iso-butyl.

In the compounds of the invention, combinations of substituents and/or variables are permissible only if such combinations result in stable compounds. As used herein, the term "stable compound" refers to a compound that is sufficiently stable to survive isolation to a useful degree of purity from a reaction mixture and formulation into a therapeutic dosage form suitable for administration.

Preferred compounds of the invention are selected from the group consisting of:

2-(1-methylethyl)-4-thiazolylmethyl-[(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimeethylethyl)amino]carbonyl]-4-(phenylmethyl)-1-piperazinyl]-2-hydroxy-1-(phenylmethyl)propyl]amino]carbonyl]-2-methylpropyl]carbamate;

2-(1-methylethyl)-4-thiazolylmethyl-(1S)-1-[[[(1S,2R)-3-[(2S)-2-[[(1,1-dimethylethyl)amino]carbonyl]-4-[(4-fluorophenyl)methyl]-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimethylethyl)amino]carbonyl]-4-(5-thienylmethyl)-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimethylethyl)amino]carbonyl]-4-[4-(3-hydroxyphenyl)methyl]-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimethylethyl)amino]carbonyl]-4-(3-pyridinylmethyl)-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimethylethyl)amino]carbonyl]-4-(4-pyridinylmethyl)-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimethylethyl)amino]carbonyl]-4-[(4- hydroxyphenyl)methyl]-1-piperazinyl]-2-hydroxy-1-(phenylmethyl)propyl]amino]carbonyl]-2-methylpropyl]carbamate;

2-(1-methylethyl)-4-thiazolylmethyl-(1S)-1-[[[(1S,2R)-3-[(2S)-4-(1H-benzimidiazol-2-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate;

2-(1-methylethyl)-4-thiazolylmethyl-[(1S)-1-[[[(1S,2R)-3-[(2S)-2-[[(1,1-dimethylethyl)amino]carbonyl]-4-(2-quinolinylmethyl)-1-piperazinyl]-2-hydroxy-1-(phenylmethyl)propyl]amino]carbonyl]-2-methylpropyl]carbamate;

2-(1-methylethyl)-4-thiazolylmethyl[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate;

N'-[(1S)-1-[[[(1S,2R)-3-[(2S)-2-[[(1,1-dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-[2-(1-methylethyl)-4-thiazolylmethyl]urea;

N'-[(1S)-1-[[[(1S,2R)-3-[(2S)-2-[[(1,1-dimethylethyl)amino]carbonyl]-4-(phenylmethyl)-1-piperazinyl]-2-hydroxy-1-(phenylmethyl)propyl]amino]carbonyl]-2-methylpropyl]-N-methyl-N-[2-(1-methylethyl)-4-thiazolylmethyl]urea;

N'-[(1S)-1-[[[(1S,2R)-3-[(2S)-2-[[(1,1-dimethylethyl)amino]carbonyl]-4-[(4-hydroxy-3-methoxyphenyl)methyl]-1-piperazinyl]-2-hydroxy-1-(phenylmethyl)propyl]amino]carbonyl]-2-methylpropyl]-N-methyl-N-[2-(1-methylethyl)-4-thiazolylmethyl]urea;

2-methyl-4-thiazolylmethyl-[(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate;

2-methyl-4-thiazolylmethyl-[(1S)-1-[[[(1S,2R)-3-[(2S)-4-[(3,4-dimethoxyphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate;

2-methyl-4-thiazolylmethyl-[(1S)-1-[[[(1S,2R)-3-[(2S)-2-[[(1,1-dimethylethyl)amino]carbonyl]-4-[(4-fluorophenyl)methyl]-1-piperazinyl]-2-hydroxy-1-(phenylmethyl)propyl]amino]carbonyl]-2-methylpropyl]carbamate;

2-ethyl-4-thiazolylmethyl-(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate;

2-(1-methylethyl)-5-thiazolylmethyl-[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate;

2-ethyl-5-thiazolylmethyl-(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate;

2-methyl-5-thiazolylmethyl-[(1S)-1-[[[(1S,2R)-3-[(2S)-4-[(3,4-dimethoxylphenyl)methyl]-2-[[(1,1-dimethylethyl)amino]carbony]-1-piperazinyl]-2-hydroxy-1-(phenylmethyl)propyl]amino]carbonyl]-2-methylpropyl]carbamate;

N'-[(1R)-1-[[[(1S,2R)-3-[(2S)-2-[[(1,1-dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-(5-thiazolylmethyl)urea;

N'-[(1S)-1-[[[(1S,2R)-3-[(2S)-2-[[(1,1-dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-(5-thiazolylmethyl)urea;

5-thiazolylmethyl-[(1S)-1-[[[(1S,2R)-3-[(2S)-2-[[(1,1-dimethylethyl)amino]carbonyl]-4-(phenylmethyl)-1-piperazinyl]-2-hydroxy-1-(phenylmethyl)propyl]amino]carbonyl]-2-methylpropyl]carbamate;

5-thiazolylmethyl-(1S)-1-[[[(1S,2R)-3-[(2S)-2-[[(1,1-dimethylethyl)amino]carbonyl]-4-(5-thiazolylmethyl)-1-piperazinyl]-2-hydroxy- 1-(phenylmethyl)propyl]amino]carbonyl]-2-methylpropyl]carbamate;

N'-[(1S)-1-[[[(1S,2R)-3-[[[(1,1-dimethylethyl)amino]carbonyl](2-methylethyl)propylamino]-2-hydroxy-1-(phenylmethyl)propyl]amino]carbonyl]-2-methylpropyl]-N-methyl-N-[2-(1-methylethyl)-4-thiazolylmethyl]urea;

2-(1-methylethyl)-4-thiazolylmethyl-[(1S)-1-[[[(1S,2R)-3-[[[(1,1-dimethylethyl)amino]carbonyl](2-methylethyl)propylamino]-2-hydroxy-1-(phenylmethyl)propyl]amino]carbonyl]-2-methylpropyl]carbamate;

2-(1-methylethyl)-4-thiazolylmethyl-(1S)-1-[[[(1S,2R)-3-[[(4-aminophenyl)sulfonyl](1-methylethyl)amino]-2-hydroxy-1-(phenylmethyl)propyl]amino]carbonyl]-2-methylpropyl]carbamate;

N'-[(1S)-1-[[[(1S,2R)-3-[[(4-aminophenyl)sulfonyl](1-methylethyl)amino]-2-hydroxy-1-(phenylmethyl)propyl]amino]carbonyl]-2-methylpropyl]-N-methyl-N-[2-(1-methylethyl)-4-thiazolylmethyl]urea;

2-(1-methylethyl)-5-thiazolylmethyl-[(1S)-1-[[[(1S,2R)-3-[(3S)-3-[[(1,1-dimethylethyl)amino]carbonyl](4aα,8aα)octahydro-2-isoquinoliny]-2-hydroxy-1-(phenylmethyl)propyl]amino]carbonyl]-2-methylpropyl]carbamate;

N'-[(1S)-1-[[[(1S,2R)-3-[(3S)-3-[[(1,1-dimethylethyl)amino]carbonyl](4aα,8aα)octahydro-2-isoquinolinyl]-2-hydroxy-1-(phenylmethyl)propyl]amino]carbonyl]-2-methylpropyl]-N-methyl-N-[2-(1-methylethyl)-5-thiazolylmethyl]urea, N'-[(1S)-1-[[[(1S,2R)-3-[(2S,4R)-2-[[(1,1-dimethylethyl)amino]carbonyl]-4-(5-thiazolylmethoxy)-1-piperidinyl]-2-hydroxy-1-(phenylmethyl)propyl]amino]carbonyl]-2-methylpropyl]-N-methyl-N-[2-(1-methylethyl)-4-thiazolylmethyl]urea;

2-(1-methylethyl)-4-thiazolylmethyl[(1S)-1-[[[(1S,2R)-3-[(2S,4R)-2-[[(1,1-dimethylethyl)amino]carbonyl]-4-(5-thiazolylmethoxy)-1-piperidinyl]-2-hydroxy-1-(phenylmethyl)propyl]amino]carbonyl]-2-methylpropyl]carbamate;

S-[2-(1-methylethyl)-4-thiazolylmethyl][(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]-carbamothioate; and 4-(1,3-benzodioxol-5-ylmethyl)-N-(1,1-dimethylethyl)-1-[(2R,3S)-3-[[(2S)-2-[[3-[2-(1-methylethyl)-4-thiazolyl]-1 -oxopropyl]amino]-3-methyl-1-oxobutyl]

amino]-2-hydroxy-4-phenylbutyl]-2-piperazinecarboxamide;
or a pharmaceutically acceptable salt, ester or prodrug thereof.

Most preferred compounds of the invention are selected from the group consisting of:

2-(1-Methylethyl)-4-thiazolylmethyl-[(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate;

2-(1-Methylethyl)-4-thiazolylmethyl-(1S)-1-[[[(1S,2R)-3-[[1(4-aminophenyl)sulfonyl](1-methylethyl)amino]-2-hydroxy-1-(phenylmethyl)propyl]amino]carbonyl]-2-methylpropyl]carbamate;

2-(1-Methylethyl)-4-thiazolylmethyl-[(1S)-1-[[[(1S,2R)-3-[(2S)-2-[[(1,1-dimethylethyl)amino]carbonyl]-4-(5-thienylmethyl)-1-piperazinyl]-2-hydroxy-1-(phenylmethyl)propyl]amino]carbonyl]-2-methylpropyl]carbamate;

2-(1-Methylethyl)-4-thiazolylmethyl[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate;

N'-[(1S)-1-[[[(1S,2R)-3-[(2S,4R)-2-[[(1,1-Dimethylethyl)amino]carbonyl]-4-(5-thiazolylmethoxy)-1-piperidinyl]-2-hydroxy-1-(phenylmethyl)propyl]amino]carbonyl]-2-methylpropyl]-N-methyl-N-[2-(1-methylethyl)-4-thiazolylmethyl]urea; and 2-(1-Methylethyl)-5-thiazolylmethyl-[(1S)-1-[[[(1S,2R)-3-[(3S)-3-[[(1,1-dimethylethy1)amino]carbonyl](4aα,8aα)octahydro-2-isoquinolinyl]-2-hydroxy-1-(phenylmethyl)propyl]amino]carbonyl]-2-methylpropyl]carbamate;

or a pharmaceutically acceptable salt, ester or prodrug thereof.

The term "alkyl" as used herein refers to straight or branched chain alkyl radicals containing from 1 to 12 carbon atoms. The term "lower alkyl" refers to straight or branched chain alkyl radicals containing from 1 to 6 carbon atoms including, but not limited to, methyl, ethyl, n-propyl, iso-propyl, n-butyl, iso-butyl, sec-butyl, t-butyl n-pentyl, 1-methylbutyl, 2,2-dimethylbutyl, 2-methylpentyl, 2,2-dimethylpropyl, n-hexyl, and the like. The alkyl groups can be unsubstituted or substituted with from one to five substituents independently selected from hydroxy, alkoxy, alkylthio, amino, alkylamino, dialkylamino and halogen. The alkyl groups can be optionally interrupted by one or more heteroatoms selected from the group consisting of oxygen, nitrogen, sulfur, and phosphorous.

The term "cycloalkyl" as used herein refers to an aliphatic ring system having 3 to 8 carbon atoms including, but not limited to, cyclopropyl, cyclopentyl, cyclohexyl, and the like.

The term "alkoxy" as used herein refers to groups having the formula —OR$^{10}$ wherein R$^{10}$ is a lower alkyl group.

The term "thioalkyl" as used herein refers to groups having the formula —SR$^{11}$ wherein R$^{11}$ is a lower alkyl group.

The term "alkylamino" as used herein refers to groups having the formula —NHR$^{12}$ wherein R$^{12}$ is a lower alkyl group.

The term "dialkylamino" as used herein refers to groups having the formula —N(R$^{13}$)$_2$ wherein each R$^{13}$ is independently a lower alkyl group.

The term "halo or halogen" as used herein refers to F, Cl, Br or I.

The term "(halo)alkyl" as used herein refers to a lower alkyl group in which one or more hydrogen atoms has been replaced with a halogen including, but not limited to, trifluoromethyl, trichloromethyl, difuoromethyl, dichloromethyl, fluoromethyl, chloromethyl, chloroethyl, 2,2-dichloroethyl and the like.

The term "aryl" as used herein refers to a mono- or bicyclic carbocyclic ring system comprising 6 to 12 carbon atoms and having one or two aromatic rings including, but not limited to, phenyl, naphthyl, tetrahydronaphthyl, indanyl, indenyl and the like. Aryl groups can be unsubstituted or substituted with from one to five substituents independently selected from hydroxy, alkoxy, alkylthio, amino, alkylamino, dialkylamino and halogen.

The term "(aryl)alkyl" as used herein refers to an aryl group as previously defined, appended to a lower alkyl radical, for example, benzyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl, bistetrahydrofuranyl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, tetrahydrofuranyl, tetrahydrothienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula:

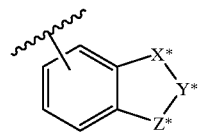

wherein X* is —CH$_2$—, —NH— or —O—, Y* is —C(O)— or [—C(R")$_2$—]$_v$ wherein R" is hydrogen or C$_1$-C$_4$-alkyl and v is 1, 2 or 3 and Z* is —O— or —NH—; such as 1,3-benzodioxolyl, 1,4-benzodioxanyl and the like.

The term "methylenedioxyphenyl" refers to a substituent having the formula:

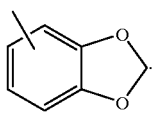

Heterocyclic groups can be unsubstituted or substituted with from one to five substituents independently selected from hydroxy, alkoxy, alkylthio, amino, alkylamino, dialkylamino and halogen. In addition, nitrogen containing heterocycles can be N-protected.

The term "(heterocyclic)alkyl" as used herein refers to a heterocyclic group appended to a lower alkyl radical including, but not limited to, pyrrolidinylmethyl, morpholinylmethyl and the like.

The term "heteroaryl" as used herein refers to an heterocyclic group containing at least one aromatic ring. Examples include groups such as, for example, furanyl, thienyl, benzothienyl, thiazolyl and the like.

The term "(heteroaryl)alkyl" as used herein refers to a heteroaryl group appended to a lower alkyl radical including, but not limited to, thienylmethyl, thienylethyl, furanylmethyl, and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis.* 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "activated carboxylic acid derivative" as used herein refers to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters, thiophenol derived esters, propylphosphonic acid derived anhydrides and the like.

The term "leaving group" as used herein refers to a group which is easily displaced from the compound, such as, for example, a halide (for example, Cl, Br or I) or a sulfonate (for example, mesylate, tosylate, triflate and the like).

As used herein, the terms "S" and "R" configuration are as defined by the IUPAC 1974 Recommendations for Section E, Fundamental Stereochemistry, Pure Appl. Chem. (1976) 45, 13–30.

The compounds of the invention can comprise asymmetrically substituted carbon atoms. As a result, all stereoisomers of the compounds of the invention are meant to be included in the invention, including racemic mixtures, mixtures of diastereomers, as well as single diastereomers of the compounds of the invention.

This invention is intended to encompass compounds having Formula I or Formula II when prepared by synthetic processes or by metabolic processes. Preparation of the compounds of the invention by metabolic processes include those occurring in the human or animal body (in vivo) or processes occurring in vitro.

The reagents required for the synthesis of the compounds of the invention are readily available from a number of commercial sources such as Aldrich Chemical Co. (Milwaukee, Wis., U.S.A.); Sigma Chemical Co. (St. Louis, Mo., U.S.A.); and Fluka Chemical Corp. (Ronkonkoma, N.Y., U.S.A.); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The compounds of the invention can be prepared as shown in Schemes I–III. As outlined in Scheme I, an N-protected (for example, with a benzyloxycarbonyl group) phenylalanylepoxide 2 is coupled with an N-protected (for example, N-Boc) piperazine compound, 1 (using, for example, 1-(3-dimethylaminopropyl)-3-ethylcarbodiimide (EDAC) ,1-hydroxybenzotriazole (HOBT), and an amine, such as, triethyl amine, and the like, in an inert solvent, for example, tetrahydrofuran, methylene chloride, and the like). The protected carboxamide product, 3, is deprotected (for example, by treatment with hydrogen gas and an hydrogenation catalyst). The amine carboxamide 3a, is then coupled with a carboxylic acid, 4,or an activated derivative thereof, using, for example, 1-(3-dimethylaminopropyl)-3-ethylcarbodiimide (EDAC),1-hydroxybenzotriazole (HOBT), and triethyl amine in an inert solvent, for example, tetrahydrofuran, methylene chloride, and the like, to provide the N-protected piperazine, 5. The piperazine is N-deprotected, (with for example, trifluoroacetic acid (TFA), and the like) and alkylated (where $X^1$ is a leaving group) to provide the final product, 6.

SCHEME I

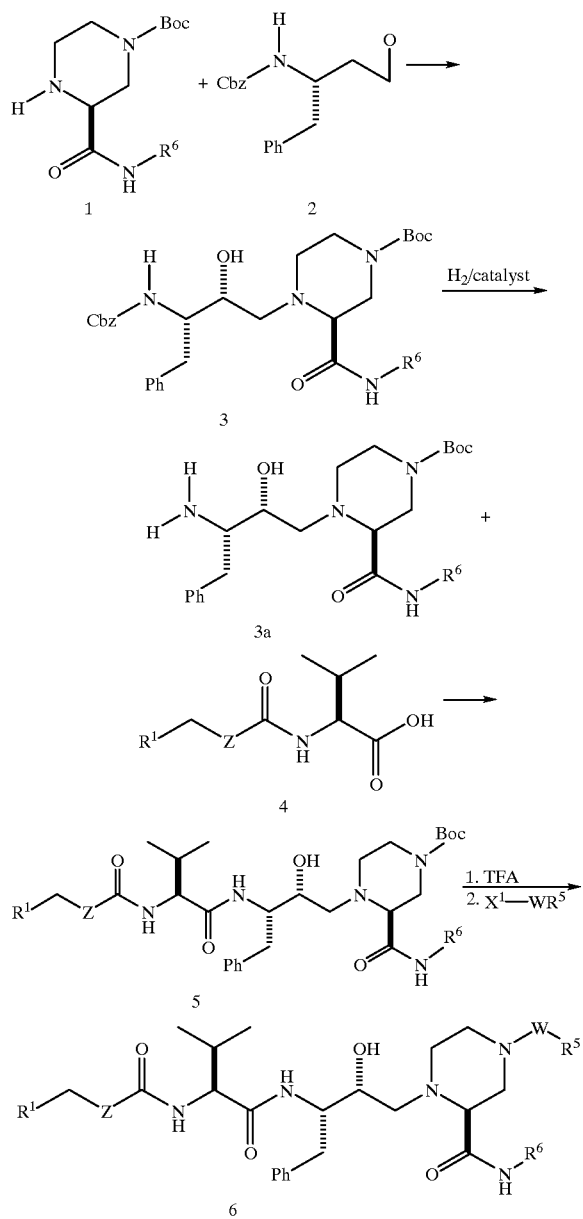

For piperidyl compounds, where Y is —CH—, the synthesis is outlined in Scheme II, shown below. A monoprotected piperidine carbamate, 7, is alkylated to provide compound 8. The alkylated carbamate is N-deprotected, (with, for example, trifluoroacetic acid, and the like), followed by coupling with the epoxide, 9, to provide carboxamide, 10. The carboxamide is N-deprotected to provide compound 10a. Compound 10a is coupled with a carboxylic acid, 4, or an activated derivative thereof, to provide the product, 11.

SCHEME II

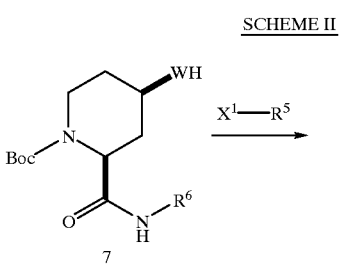

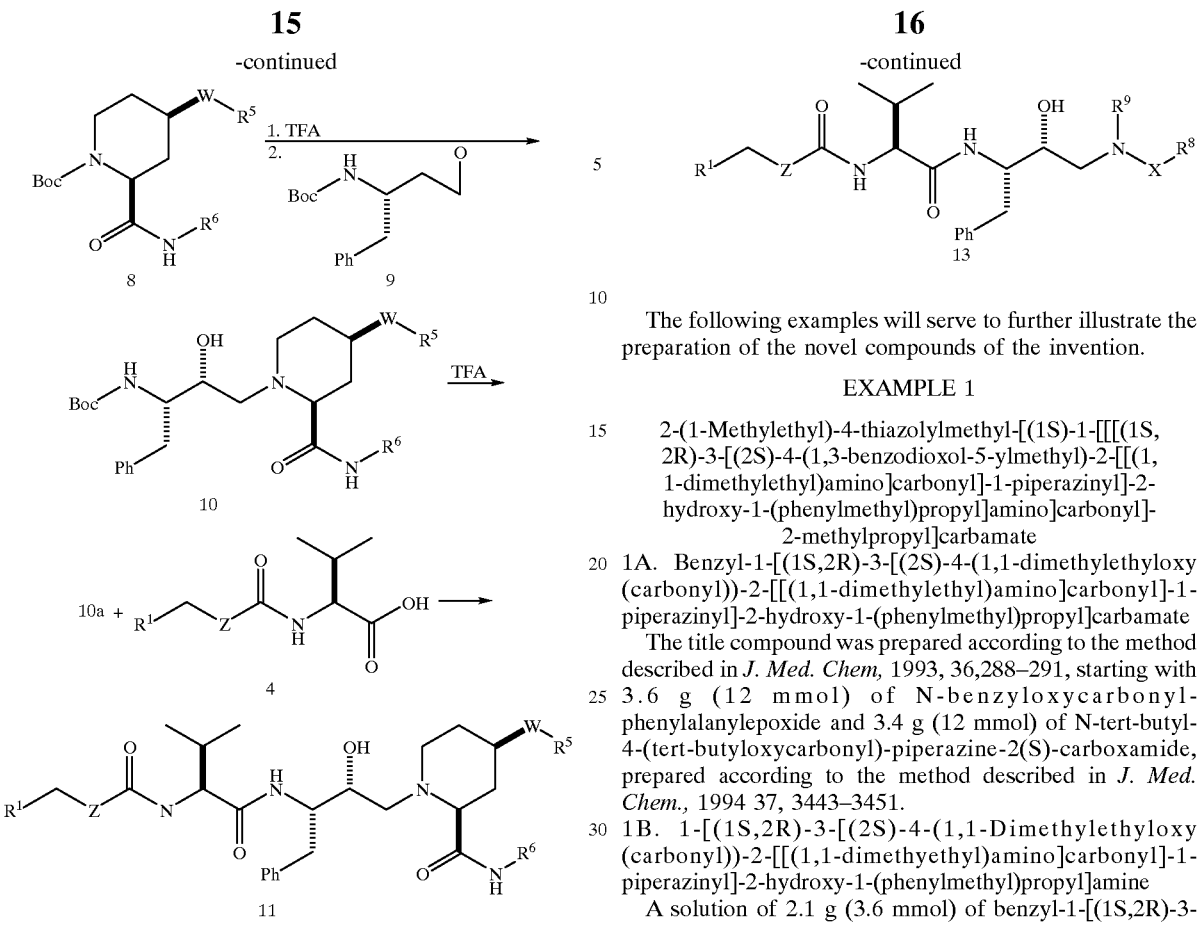

The synthesis of compounds of the invention having the —N(R⁹)—X—R⁸ group, is outlined in Scheme III., Urea, 12, prepared according to the description in *J. Med. Chem.,* 1993, 36, 288–291, is coupled with a carboxylic acid, 4, or an activated derivative thereof, using, for example, 1-(3-dimethylaminopropyl)-3-ethylcarbodiimide (EDAC), 1-hydroxybenzotriazole (HOBT), and triethyl amine in an inert solvent, for example, tetrahydrofuran, methylene chloride, and the like, to provide the product 13.

SCHEME III

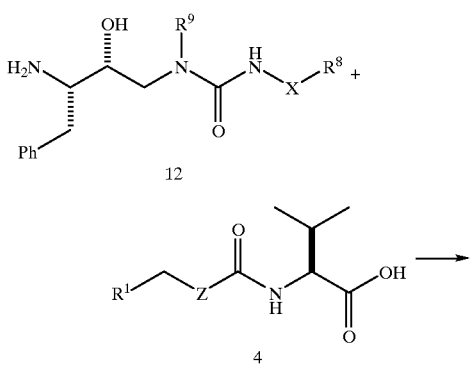

The following examples will serve to further illustrate the preparation of the novel compounds of the invention.

EXAMPLE 1

2-(1-Methylethyl)-4-thiazolylmethyl-[(1S)-1-[[[(1S, 2R)-3-[(2S)-4-(1,3-benzodioxol-5-ylmethyl)-2-[[(1, 1-dimethylethyl)amino]carbonyl]-1-piperazinyl]-2-hydroxy-1-(phenylmethyl)propyl]amino]carbonyl]-2-methylpropyl]carbamate 1A. Benzyl-1-[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]carbamate The title compound was prepared according to the method described in *J. Med. Chem,* 1993, 36,288–291, starting with 3.6 g (12 mmol) of N-benzyloxycarbonyl-phenylalanylepoxide and 3.4 g (12 mmol) of N-tert-butyl-4-(tert-butyloxycarbonyl)-piperazine-2(S)-carboxamide, prepared according to the method described in *J. Med. Chem.,* 1994 37, 3443–3451.

1B. 1-[(1S,2R)-3-[(2S)-4-(1,1-Dimethylethyloxy(carbonyl))-2-[[(1,1-dimethyethyl)amino]carbonyl]-1-piperazinyl]-2-hydroxy-1-(phenylmethyl)propyl]amine A solution of 2.1 g (3.6 mmol) of benzyl-1-[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]carbamate in 20 ml of methanol was treated with hydrogen, at greater than 1 atmosphere, in the presence of Pd/C (50 mg; 10%), and stirred for 2 hours. The catalyst was removed via filtration over a celite pad and the solvent was evaporated at reduced pressure to provide the title compound as a yellow oil (yield: 1.6 g; 99%).

1C. 2-(1-Methylethyl)-4-thiazolylmethyl-(1S)-1-[[[(1S,2R)-3-[(2S)-4(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl] carbamate A solution of 1.5 g (3.3 mmol) of 1-[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amine in 7 ml of tetrahydrofuran (THF) and 7 ml of methylene chloride was prepared and treated with 1.0 g (3.3 mmol) of [(2-isopropyl-4-thiazolyl)methyloxycarbonyl]-L-valine, 642 mg (3.3 mmol) of 1-(3-dimethylaminopropyl)-3-ethylcarbodiimide (EDAC), 45 mg (0.33 mmol) of 1-hydroxybenzotriazole (HOBT), and 466 µl (3.3 mmol) of triethyl amine. The solution was stirred at room temperature for 6 hours, and concentrated in vacuo. The residue was taken up with ethyl acetate, washed with equal portions of 3 N HCl solution, 10% aqueous NaHCO₃ (20 mL), saturated brine, and dried over MgSO₄. The product was concentrated in vacuo and purified by chromatography on silica gel, using 5% methanol:methylene chloride, to provide the title compound (yield: 2 .4 g, 98%). MS: 731 (M+H)⁺.

¹H NMR (DMSO-d₆) δ1.08 (d, J=7 Hz, 6H), 2.78 (heptet, J=7 Hz, 1H), 9.06 (br s, 1H), 9.30 (br s, 1H).

1D. 2-(1-Methylethyl)-4-thiazolylmethyl-(1S)-1-[[[(1S, 2R)-3-[(2S)-2-[[(1,1-dimethylethyl)amino]carbonyl]-1-piperazinyl]-2-hydroxy-1-(phenylmethyl)propyl]-amino]carbonyl]-2-methylpropyl]carbamate A solution of 2.4 g (3.2 mmol) of 2-(1-methylethyl)-4-thiazolylmethyl-(1S)-1-[[[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl]carbamate in 20 ml of dichloromethane was prepared and treated with 2 ml of trifluoroacetic acid. The reaction was monitored by TLC. After the reaction was completed, the solvent was removed at reduced pressure. The residue was dissolved in methylene chloride, washed with saturated aqueous NaHCO₃ and saturated brine. The organic layer was dried over Na₂SO₄ and concentrated in vacuo to provide the title compound as a light yellow oil (yield: 2.0 g; 90%).

1E. 2-(1-Methylethyl)-4-thiazolylmethyl-[(1S)-1-[[[(1S, 2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate A solution of 514 mg (0.82 mmol) of 2-(1-methylethyl)-4-thiazolylmethyl-(1S)-1-[[[(1S,2R)-3-[(2S)-2-[[(1,1-dimethylethyl)amino]carbonyl]-1-piperazinyl]-2-hydroxy-1-(phenylmethyl)propyl]amino]carbonyl]-2-methylpropyl]carbamate in 5 ml of dimethylformamide (DMF) was prepared and treated with 140 mg (0.8 mmol) of 3,4-dioxomethylenebenzyl chloride followed by 284 μl (1.6 mmol) of N,N-diisopropyl ethyl amine, stirred at room temperature over night, and partitioned between ethyl acetate and saturated sodium bicarbonate solution. The organic layer was washed with brine, dried over sodium sulfate, and concentrated in vacuo. The residue was purified by chromatography on silica gel, using 5% methanol:methylene chloride, to provide the title compound (yield: 502 mg; 81%).

MS: 765 (M+H)⁺.

¹H NMR (CDCl₃) δ0.67 (d, J=6.3 Hz, 3H), 0.83 (d, J=6.3 Hz, 3H), 1.37 (s, 9H), 1.41 (t, J=7.5, 6H), 2.05 (hexlet, J=6.0 Hz, 1H), 2.26 (m, 1H), 2.41 (m, 1H), 2.58 (m, 2H), 2.73 (m, 3H), 2.83 (m, 2H), 2.90 (m, 1H), 3.33 (AB, J=1.50 Hz, 2H), 3.46 (s, 2H), 3.80 (m, 1H), 3.93 (m, 1H), 4.22 (septet, J=4.5 Hz, 1H), 5.08 (m, 1H), 5.17 (d, J=4.5 Hz, 2H), 5.97 (s, 2H), 6.13 (d, J=9.0 Hz, 1H), 6.71 (s, 1H), 6.75 (s, 2H), 7.12–7.22 (m, 7H), 8.19 (br s, 1H).

EXAMPLE 2

2-(1-Methylethyl)-4-thiazolylmethyl-[(1S)-1-[[[(1S, 2R)-3-[(2S)-2-[[(1,1-dimethylethyl)amino]carbonyl]-4-(phenylmethyl)-1-piperazinyl]-2-hydroxy-1-(phenylmethyl)propyl]amino]carbonyl]-2-methylpropyl]carbamate The title compound was prepared according to the method described in Example 1E, substituting benzyl bromide in place of 3,4-dioxomethylenebenzyl chloride.

MS: 721 (M+H)⁺.

¹H NMR (CDCl₃) δ0.68 (d, J=6.3 Hz, 3H), 0.84 (d, J=6.3 Hz, 3H), 1.36 (s, 9H), 1.40 (d, J=6.3, 6H), 2.04 (hextet, J=6.0 Hz, 1H), 2.28 (dt, J=9.3, 3.3 Hz, 1H), 2.45 (dt, J=12.0, 3.0 Hz, 1H), 2.58 (m, 2H), 2.75 (m, 2H), 2.88 (m, 2H), 3.33 (heptet, J=6.3 Hz, 1H), 3.37 (m, 1H), 3.46 (s, 2H), 3.79 (m, 1H), 3.85 (dd, J=8.4, 6.0 Hz, 1H), 4.22 (septet, J=4.5 Hz, 1H), 5.11 (dd, J=10.8, 7.5 Hz, 1H), 5.17 (d, J=3.3 Hz, 2H), 6.13 (d, J=9.0 Hz, 2H), 7.12–7.33 (m, 11H), 8.02 (s, 1H), 8.26 (br s, 1H).

EXAMPLE 3

2-(1-Methylethyl)-4-thiazolylmethyl-(1S)-1-[[[(1S, 2R)-3-[(2S)-2-[[(1,1-dimethylethyl)amino]carbonyl]-4-[(4-fluorophenyl)methyl]-1-piperazinyl]-2-hydroxy-1-(phenylmethyl)propyl]amino]carbonyl]-2-methylpropyl]carbamate The title compound was prepared according to the method described in Example 1E, substituting 4-fluorobenzyl chloride in place of 3,4-dioxomethylenebenzyl chloride.

MS: 739 (M+H)⁺.

¹H NMR (CDCl₃) δ0.67 (d, J=6.3 Hz, 3H), 0.84 (d, J=6.3 Hz, 3H), 1.35 (s, 9H), 1.41 (d, J=7.5, 6H), 2.06 (hextet, J=6.0 Hz, 1H), 2.30 (m, 1H), 2.48 (m, 1H), 2.59 (m, 1H), 2.73 (m, 2H), 2.83 (m, 2H), 2.92 (m, 2H), 3.33 (AB, J=1.50 Hz, 2H), 3.37 (m, 1H), 3.44 (s, 2H), 3.83 (m, 2H), 4.22 (m, 1H), 5.09 (m, 1H), 5.17 (d, J=4.8 Hz, 2H), 6.19 (d, J=9.0 Hz, 1H), 7.03 (d, J=8.4 Hz, 1H), 7.12–7.22 (m, 9H), 8.09 (br s, 1H).

EXAMPLE 4

2-(1-Methylethyl)-4-thiazolylmethyl-[(1S)-1-[[[(1S, 2R)-3-[(2S)-2-[[(1,1-dimethylethyl)amino]carbonyl]-4-(5-thienylmethyl)-1-piperazinyl]-2-hydroxy-1-(phenylmethyl)propyl]amino]carbonyl]-2-methylpropyl]carbamate The title compound was prepared according to the method described in Example 1E, substituting 5-(chloromethyl)thiazole in place of 3,4-dioxomethylenebenzyl chloride.

MS: 728 (M+H)⁺.

¹H NMR (CDCl₃) δ0.68 (d, J=6.3 Hz, 3H), 0.83 (d, J=6.3 Hz, 3H), 1.38 (s, 9H), 1.41 (d, J=7.5, 6H), 2.06 (hextet, J=6.0 Hz, 1H), 2.33 (m, 1H), 2.58 (m, 2H), 2.73 (m, 2H), 2.83 (m, 2H), 2.90 (m, 1H), 3.33 (heptet, J=4.5 Hz, 1H), 3.36 (m, 1H), 3.73 (d, J=3.0 Hz, 2H), 3.80 (m, 1H), 3.83 (dd, J=7.5, 6.0 Hz, 1H), 4.22 (septet, J=4.5 Hz, 1H), 5.07 (d, J=7.5 Hz, 1H), 5.17 (d, J=4.5 Hz, 2H), 6.15 (d, J=7.5 Hz, 1H), 7.12–7.22 (m, 8H), 7.40 (m, 1H), 7.73 (s, 1H), 7.79 (s, 1H), 8.80 (s, 1H).

EXAMPLE 5

2-(1-Methylethyl)-4-thiazolylmethyl-[(1S)-1-[[[(1S, 2R)-3-[(2S)-2-[[(1,1-dimethylethyl)amino]carbonyl]-4-[4-(3-hydroxyphenyl)methyl]-1-piperazinyl]-2-hydroxy-1-(phenylmethyl)propyl]amino]carbonyl]-2-methylpropyl]carbamate The title compound was prepared according to the method described in Example 1E, substituting 3-hydroxybenzyl chloride in place of 3,4-dioxomethylenebenzyl chloride.

MS: 737 (M+H)⁺.

¹H NMR (CDCl₃) δ0.67 (d, J=6.3 Hz, 3H), 0.83 (d, J=6.3 Hz, 3H), 0.96 (m, 1H), 1.37 (s, 9H), 1.40 (d, J=7.5, 6H), 2.03 (hextet, J=6.0 Hz, 1H), 2.32 (m, 1H), 2.45 (m, 1H), 2.61 (m, 2H), 2.76 (m, 2H), 2.85 (m, 2H), 2.89 (m, 2H), 3.32 (m, 1H), 3.37 (s, 1H), 3.42 (m, 1H), 3.61 (t, J=8.4 Hz, 1H), 3.87 (m, 2H), 4.22 (m, 1H), 4.63 (s,1H), 5.16 (s, 2H), 6.36 (m, 1H), 6.78 (d, J=7.5 Hz, 2H), 7.12–7.22 (m, 9H), 8.19 (br s, 1H).

EXAMPLE 6

2-(1-Methylethyl)-4-thiazolylmethyl-[(1S)-1-[[[(1S, 2R)-3-[(2S)-2-[[(1,1-dimethylethyl)amino]carbonyl]-4-(3-pyridinylmethyl)-1-piperazinyl]-2-hydroxy-1-(phenylmethyl)propyl]amino]carbonyl]-2-methylpropyl]carbamate The title compound was prepared according to the method described in Example 1E, substituting 3-picolyl chloride hydrochloride in place of 3,4-dioxomethylenebenzyl chloride.

MS: 722 (M+H)+.

¹H NMR (CDCl) δ0.68 (d, J=6.3 Hz, 3H), 0.83 (d, J=6.3 Hz, 3H), 1.36 (s, 9H), 1.41 (d, J=7.5 Hz, 6H), 2.06 (Hextet, J=4.5 Hz, 1H), 2.47 (m, 1H), 2.60 (m, 2H), 2.71 (m, 2H), 2.81 (m, 1H), 2.83 (m, 2H), 2.92 (m, 1H), 3.34 (heptet, J=4.5 Hz, 1H), 3.35 (m, 1H), 3.51 (s, 2H), 3.81 (m, 1H), 3.85 (m, 1H), 4.22 (m, 1H), 4.75 (m, 1H), 5.07 (d, J=9.0 Hz, 1H), 5.17 (d, J=7.8 Hz, 2H), 6.15 (d, J=7.8 Hz, 1H), 7.12–7.22 (m, 8H), 7.61 (d, J=7.8 Hz, 1H), 7.89 (br s, 1H), 8.55 (d, J=3 Hz, 1H), 8.56 (d, J=6.0 Hz, 1H).

EXAMPLE 7

2-(1-Methylethyl)-4-thiazolylmethyl-[(1S)-1-[[[(1S, 2R)-3-[(2S)-2-[[(1,1-dimethylethyl)amino] carbonyl]-4-(4-pyridinylmethyl)-1-piperazinyl]-2-hydroxy-1-(phenylmethyl)propyl]amino]carbonyl]-2-methylpropyl]carbamate The title compound was prepared according to the method described in Example 1E substituting 4-picolyl chloride hydrochloride in place of 3,4-dioxomethylenebenzyl chloride.

MS: 722 (M+H)+.

¹H NMR (CDCl₃) δ0.65 (d, J=6.3 Hz, 3H), 0.94 (d, J=6.3 Hz, 3H), 1.37 (s, 9H), 1.41 (d, J=7.5, 6H), 2.07 (hex let, J=6.0 Hz, 1H), 2.37 (m, 1H), 2.57 (m, 1H), 2.62 (m, 2H), 2.69 (m, 2H), 2.81 (m, 2H), 2.91 (m, 1H), 3.32 (m, 1H), 3.34 (m, 1H), 3.49 (AB, J=15.0 Hz, 2H), 3.80 (m, 1H), 3.85 (m, 1H), 4.21 (m,1H), 4.62 (m, 1H), 5.06 (d, J=7.5 Hz, 1H), 5.14 (m, 1H), 5.17 (d, J=4.5 Hz, 2H), 6.14 (d, J=8.4 Hz, 1H), 7.12–7.22 (m, 8H), 7.77 (br s, 1H), 8.08 (d, J=6.0 Hz, 2H).

EXAMPLE 8

2-(1-Methylethyl)-4-thiazolylmethyl-[(1S)-1-[[[(1S, 2R)-3-[(2S)-2-[[(1,1-dimethylethyl)amino] carbonyl]-4-[(4-hydroxyphenyl)methyl]-1-piperazinyl]-2-hydroxy-1-(phenylmethyl)propyl] amino]carbonyl]-2-methylpropyl]carbamate The title compound was prepared according to the method described in Example 1E, substituting 4-hydroxybenzyl chloride hydrochloride in place of 3,4-dioxomethylenebenzyl chloride.

MS: 737 (M+H)+.

¹H NMR (CDCl₃) δ0.68 (d, J=6.3 Hz, 3H), 0.83 (d, J=6.3 Hz, 3H), 1.35 (s, 9H), 1.41 (d, J=7.5, 6H), 2.03 (hextet, J=4.5 Hz, 1H), 2.27 (dt, J=7.5, 3.0 Hz, 1H), 2.36 (dd, J=12.0, 3.0 Hz, 1H), 2.59 (m, 2H), 2.74 (m, 2H), 2.87 (m, 2H), 2.79 (m,1H), 2.92 (m, 1H), 3.32 (m, 1H), 3.33 (AB, J=15.0 Hz, 2H), 3.40 (m, 2H), 3.72 (m, 1H), 3.78 (dd, J=8.4, 6.0 Hz, 1H), 4.22 (septet, J=4.5 Hz, 1H), 5.22 (d, J=4.5 Hz, 2H), 5.23 (m, 1H), 6.17 (m, 1H), 6.40 (d, J=9.0 Hz, 1H), 6.80 (d, J=8.7 Hz, 2H), 7.09–7.21 (m, 8H), 8.31 (br s, 1H).

EXAMPLE 9

2-(1-Methylethyl)-4-thiazolylmethyl-(1S)-1-[[[(1S, 2R)-3-[(2S)-4-(1H-benzimidiazol-2-ylmethyl)-2-[[(1,1-dimethylethyl)amino]carbonyl]-1-piperazinyl]-2-hydroxy-1-(phenylmethyl)propyl] amino]carbonyl]-2-methylpropyl]carbamate The title compound was prepared according to the method described in Example 1E, substituting 2-(chloromethyl) benzimidazole in place of 3,4-dioxomethylenebenzyl chloride.

MS: 761 (M+H)+.

¹H NMR (CDCl₃) δ0.62 (d, J=6.3 Hz, 3H), 0.83 (d, J=6.3 Hz, 3H), 1.41 (d, J=7.5, 6H), 1.43 (s, 9H), 2.11 (hextet, J=4.5 Hz, 1H), 2.52 (m, 1H), 2.57 (dd, J=12.0, 3.0 Hz, 1H), 2.72 (m, 2H), 2.79 (m, 3H), 3.02 (dd, J=15.0, 4.5 Hz, 1H), 3.17 (m, 3H), 3.34 (heptet, J=4.5 Hz, 1H), 3.85 (m, 2H), 3.95 (d, J=9.0 Hz, 1H), 4.25 (m, 1H), 4.98 (m, 1H), 5.13 (s, 2H), 5.17 (m, 1H), 6.17 (m, 1H), 7.12–7.28 (m, 11H), 7.63 (m, 2H).

EXAMPLE 10

2-(1-Methylethyl)-4-thiazolylmethyl-[(1S)-1-[[[(1S, 2R)-3-[(2S)-2-[[(1,1-dimethylethyl)amino] carbonyl]-4-(2-quinolinylmethyl)-1-piperazinyl]-2-hydroxy-1-(phenylmethyl)propyl]amino]carbonyl]-2-methylpropyl]carbamate The title compound was prepared according to the method described in Example 1E, substituting 2-(chloromethyl) quinoline monohydrochloride in place of 3,4-dioxomethylenebenzyl chloride.

MS: 772 (M+H)+.

¹H NMR (CDCl₃) δ0.67 (d, J=6.3 Hz, 3H), 0.83 (d, J=6.3 Hz, 3H), 1.37 (s, 9H), 1.40 (d, J=7.5, 6H), 2.05 (hextet, J=6.0 Hz, 1H), 2.50 (m, 1H), 2.61 (m, 2H), 2.70 (m, 1H), 2.71 (m, 2H), 2.85 (m, 2H), 2.92 (m, 1H), 3.32 (m, 1H), 3.47 (m, 1H), 3.82 (m, 2H), 3.85 (m, 1H), 4.22 (septet, J=4.5 Hz, 1H), 4.79 (s, 1H), 5.10 (m, 1H), 5.17 (d, J=8.4 Hz, 2H), 6.11 (s, 1H), 7.12–7.22 (m, 9H), 7.47 (d, J=6.6 Hz, 1H), 7.56 (t, J=7.5 Hz, 1H), 7.73 (t, J=8.4 Hz, 1H), 7.83 (d, J=8.4 Hz, 1H), 8.07 (d, J=7.5 Hz, 1H), 8.17(d, J=8.4 Hz, 1H).

EXAMPLE 11

2-(1-Methylethyl)-4-thiazolylmethyl[(1S)-1-[[[(1S, 2R)-3-[(2S)-4-[(3,4-dimethoxylphenyl)methyl]-2-[[(1,1-dimethylethyl)aminocarbonyl]-1-piperazinyl]-2-hydroxy-1-(phenylmethyl)propyl] amino]carbonyl]-2-methylpropyl]carbamate The title compound was prepared according to the method described in Example 1E, substituting 3,4-dimethoxy benzyl chloride in place of 3,4-dioxomethylenebenzyl chloride.

MS: 781 (M+H)+.

¹H NMR (CDCl₃)δ0.68 (d, J=6.3 Hz, 3H), 0.84 (d, J=6.3 Hz, 3H), 1.35 (s, 9H), 1.41 (d, J=6.3, 6H), 2.05 (hextet, J=6.0 Hz, 1H), 2.25 (m, 1H), 2.45 (m, 1H), 2.58 (m, 2H), 2.74 (m, 3H), 2.84 (m, 2H), 2.90 (m, 1H), 3.35 (heptet, J=6.3 Hz, 1H), 3.40 (AB, J=15.0 Hz, 2H), 3.81 (m, 1H), 3.87 (s, 3H), 3.88 (s, 3H), 4.21 (m, 1H), 5.08 (m, 1H), 5.17 (d, J=3.3 Hz, 2H), 6.12 (m, 1H), 6.26 (s, 1H), 6.82 (s, 2H), 7.10–7.22 (m, 8H), 8.21 (brs, 1H).

EXAMPLE 12

N'-[(1S)-1-[[[1(1S,2R)-3-[(2S)-2-[[(1,1-Dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-[2-(1-methylethyl)-4-thiazolylmethyl]urea 12A. N'-[(1S)-1-[[[(1S,2R)-3-[(2S)-2-[[(1,1-Dimethylethyl)amino]carbonyl]-4-(1,1-dimethylethyloxy(carbonyl))-1-1-piperazinyl]-2-hydroxy-1-(phenylmethyl)propyl]amino] carbonyl]-2-methylpropyl]-N-methyl-N-[2-(1-methylethyl)-4-thiazolmethyl]urea A solution of 1.5 g (3.3 mmol) of 1-[(1S,2R)-3-[(2S)-4-(1,1-dimethylethyloxy(carbonyl))-2-[[(1,1-dimethylethyl)

amino]carbonyl]-1-piperazinyl]-2-hydroxy-1-(phenylmethyl)propyl]amine in 7 ml of THF and 7 ml of methylene chloride was prepared and treated with 1.0 g (3.3 mmol) of N-methyl-N-[(((2-isopropyl-4-thiazolyl)methyl)amino)carbonyl]-L-valine, 642 mg (3.3 mmol) of EDAC, 45 mg (0.33 mmol) of HOBT, and 466 µl (3.3 mmol) of triethyl amine. The solution was stirred at room temperature for 6 hours, and concentrated in vacuo. The residue was taken up with ethyl acetate, washed with equal portions (15 ml) of 3 N HCl solution, 10% aqueous NaHCO$_3$, and saturated brine. The organic layer was dried over MgSO$_4$ and concentrated in vacuo. The mixture was purified by chromatography on silica gel using 5% methanol:methylene chloride to provide the title compound (yield: 2.4 g; 98%).

12B. N'-[(1S)-1-[[[(1S,2R)-3-[(2S)-2-[[(1,1-Dimethylethyl)amino]carbonyl]-1-piperazinyl]-2-hydroxy-1-(phenylmethyl)propyl]amino]carbonyl]-2-methylpropyl]-N-methyl-N-[2-(1-methylethyl)-4-thiazolylmethyl]urea A solution of 2.4 g (3.2 mmol) of N'-[(1S)-1-[[[(1S,2R)-3-[(2S)-2-[[(1,1-dimethylethyl)amino]carbonyl]-4-(1,1-dimethylethyloxy(carbonyl))-1-piperazinyl]-2-hydroxy-1-(phenylmethyl)propyl]amino]carbonyl]-2-methylpropyl]-N-methyl-N-[2-(1-methylethyl)-4-thiazolylmethyl]urea in 20 ml of dichloromethane, was prepared and treated with 2 ml of trifluoroacetic acid. The reaction was monitored by TLC. After the reaction was completed, the solvent was removed at reduced pressure. The residue was dissolved in methylene chloride, washed with saturated aqueous NaHCO$_3$, and saturated brine. The organic layer was dried over Na$_2$SO$_4$ and concentrated in vacuo to provide the title compound as a light oil (yield: 2.0 g; 90%). The product was used in Example 12C without further purification.

12C. N'-[(1S)-1-[[[(1S,2R)-3-[(2S)-2-[[(1,1-Dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-[2-(1-methylethyl)-4-thiazolylmethyl]urea The title compound was prepared according to the method described in Example 1E, starting with the product, prepared in Example 12B, and substituting 5-thiazolylmethyl chloride in place of 3,4-dioxomethylenebenzyl chloride.

MS: 741 (M+H)$^+$.

$^1$H NMR (CDCl$_3$) δ0.75 (d, J=6.3 Hz, 3H), 0.89 (d, J=6.3 Hz, 3H), 1.33 (d, J=3.0 Hz, 3H), 1.45 (d, J=3.0 Hz, 3H), 1.47 (s, 9H), 2.18 (m, 1H), 2.40 (dt, J=7.5, 3.0 Hz, 1H), 2.55 (m, 1H), 2.62 (m, 4H), 2.73 (dd, J=15.0, 4.5 Hz, 2H), 2.89 (m, 1H), 2.95 (s, 3H), 3.22 (heptet, J=6.0 Hz, 1H), 3.27 (d, J=3.0 Hz, 2H), 3.73 (d, J=3.0 Hz, 2H), 3.87 (m, 1H), 3.99 (dd, J=6.3, 6.0 Hz, 1H), 4.16 (septet, J=4.5 Hz, 1H), 4.37 (s, 2H), 4.61 (br s, 1H), 6.00 (br s, 1H), 6.39 (d, J=9.0 Hz, 1H), 6.97 (s, 1H), 7.08–7.17 (m, 5H), 7.54 (s, 1H), 7.72 (s, 1H), 8.79 (s,1H).

EXAMPLE 13

N'-[(1S)-1-[[[(1S,2R)-3-[(2S)-2-[[(1,1-Dimethylethyl)amino]carbonyl]-4-(phenylmethyl)-1-piperazinyl]-2-hydroxy-1-(phenylmethyl)propyl]amino]carbonyl]-2-methylpropyl]-N-methyl-N-[2-(1-methylethyl)-4-thiazolylmethyl]urea The title compound was prepared according to the method described in Example 12C, substituting benzyl bromide in place of 5-thiazolylmethyl chloride.

MS: 734 (M+H)$^+$.

$^1$H NMR (CDCl$_3$) δ0.75 (d, J=6.3 Hz, 3H), 0.88 (d, J=6.3 Hz, 3H), 1.45 (d, J=7.5 Hz, 6H), 1.46 (s, 9H), 2.15 (hextet, J=6.3 Hz, 1H), 2.32 (dt, J=9.0, 3.0 Hz, 1H), 2.51 (dd, J=8.4, 3.0 Hz, 1H), 2.59 (dd, J=8.4, 3.0 Hz, 1H), 2.70 (m, 2H), 2.78 (m, 2H), 2.95 (s, 3H), 3.24 (heptet, J=7.5 Hz, 1H), 3.32 (t, J=3.0 Hz, 1H), 3.45 (s, 2H), 3.81 (m,1H), 4.01 (dd, J=7.5, 6.0 Hz, 1H), 4.17 (septet, J=4.5 Hz, 1H), 4.48 (s, 2H), 4.84 (br s, 1H), 5.89 (m, 1H), 6.48 (d, J=9.0 Hz, 1H), 6.95 (s, 1H), 7.07–7.18 (m, 5H), 7.25–7.34 (m, 5H), 8.04 (brs, 1H).

EXAMPLE 14

N'-[(1S)-1-[[[(1S,2R)-3-[(2S)-2-[[(1,1-Dimethylethyl)amino]carbonyl]-4-[(4-hydroxy-3-methoxyphenyl)methyl]-1-piperazinyl]-2-hydroxy-1-(phenylmethyl)-propyl]amino]carbonyl]-2-methylpropyl]-N-methyl-N-[2-(1-methylethyl)-4-thiazolylmethyl]urea The title compound was prepared according to the method described in Example 12C substituting 3-methoxy-4-hydroxybenzyl chloride in place of 5-thiazolylmethyl chloride.

MS: 780 (M+H)$^+$.

$^1$H NMR (CDCl$_3$) δ0.76 (d, J=6.3 Hz, 3H), 0.88 (d, J=6.3 Hz, 3H), 1.35 (s, 9H), 1.36 (d, J=7.5, 6H), 2.17 (hextet, J=6.0 Hz, 1H), 2.31 (dt, J=7.5, 3.0 Hz, 1H), 2.53 (m, 2H), 2.63 (m, 2H), 2.78 (m, 2H), 2.91 (m, 1H), 2.96 (s, 3H), 3.26 (q, J=7.5 Hz, 2H), 3.29 (m, 1H), 3.38 (AB, J=15.0 Hz, 2H), 3.83 (m, 1H), 3.89 (s, 3H), 4.01 (dd, J=7.5, 6.0 Hz, 1H), 4.17 (septet, J=4.5 Hz, 1H), 4.38 (s, 2H), 4.77 (m, 1H), 5.58 (s, 1H), 5.92 (m, 1H), 6.38 (d, J=9.0 Hz, 1H), 6.77 (m, 2H), 6.87 (d, J=8.4 Hz, 1H), 6.96 (s, 1H), 7.12–7.22 (m, 6H), 7.96 (br s, 1H).

EXAMPLE 15

2-Methyl-4-thiazolylmethyl-[(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate 15A. 2-Methyl-4-thiazolylmethyl-[(1S)-1-[[[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl]carbamate The title compound was prepared according to the method of Example 1C substituting [(2-methyl-4-thiazolyl)methyloxycarbonyl]-L-valine in place of [(2-isopropyl-4-thiazolyl)methyloxycarbonyl]-L-valine. This was followed by treatment of the product with trifluoroacetic acid according to the method of Example 1D.

15B. 2-Methyl-4-thiazolylmethyl-[(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamate A solution of 98 mg (0.16 mmol) of 2-methyl-4-thiazolylmethyl-[(1S)-1-[[[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl]carbamate in 1 ml of DMF was treated with 30 mg (0.18 mmol) of 3,4-dioxomethylenebenzyl chloride followed by 43 µl (0.24 mmol) of N,N-diisopropyl ethyl amine. The solution was stirred at room temperature over night. After stirring, the solution was partitioned between ethyl acetate and saturated sodium bicarbonate solution. The organic solution was washed with brine, dried over sodium sulfate, and concentrated in vacuo. The mixture was purified by chromatography on silica gel, using 5% methanol:methylene chloride, to provide the title compound (yield: 31 mg; 26%).

MS: 737 (M+H)+.

¹H NMR (CDCl₃) δ 0.67 (d, J=6.3 Hz, 3H), 0.84 (d, J=6.3 Hz, 3H), 1.37 (s, 9H), 2.05 (hextet, J=4.5 Hz, 1H), 2.26 (m, 1H), 2.41 (dd, J=12.0, 3.0 Hz, 1H), 2.55 (m, 1H), 2.59 (dd, J=9.3, 3.0 Hz, 2H), 2.72 (m, 2H), 2.73 (s, 3H), 2.76 (m, 1H), 2.83 (m, 2H), 2.91 (m, 1H), 3.35 (m, 1H), 3.47 (s, 2H), 3.79 (m, 1H), 3.86 (dd, J=7.5, 6.0 Hz, 1H), 4.22 (m, 1H), 4.93 (m, 1H), 5.62 (m, 2H), 5.65 (d, J=3.0 Hz, 2H), 5.96 (s, 2H), 6.18 (d, J=9.0 Hz, 1H), 6.70 (d, J=7.5 Hz, 1H), 6.75 (s, 1H), 6.78 (d, J=7.5 Hz, 1H), 7.12–7.22 (m, 6H), 8.19 (br s, 1H).

EXAMPLE 16

2-Methyl-4-thiazolylmethyl-[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate The title compound was prepared according to the method described in Example 15B, substituting 3,4-dimethoxybenzyl chloride in place of 3,4-dioxomethylenebenzyl chloride.

MS: 753 (M+H)+.

¹H NMR (DMSO-d₆) δ 0.67 (d, J=6.3 Hz, 3H), 0.69 (d, J=6.3 Hz, 3H), 1.23 (s, 9H), 1.78 (hextet, J=4.5 Hz, 1H), 2.22 (m, 2H), 2.27 (m, 1H), 2.32 (m, 1H), 2.53 (m, 3H), 2.63 (s, 3H), 2.67 (m, 1H), 2.87 (m, 2H), 2.98 (m, 1H), 3.33 (m, 3H), 3.63 (m, 1H), 3.72 (s, 3H), 3.73 (s, 3H), 4.05 (m, 1H), 4.86 (d, J=9.0 Hz, 1H), 5.00 (s, 2H), 6.79 (d, J=7.5 Hz, 1H), 6.87 (s, 1H), 6.89 (d, J=7.5 Hz, 1H), 7.10 (d, J=6.0 Hz, 2H), 7.18 (d, J=6.3 Hz, 2H), 7.26 (d, J=7.5 Hz, 2H), 7.41 (s, 1H), 7.53 (s, 1H), 7.67 (d, J=9.0 Hz, 1H).

EXAMPLE 17

2-Methyl-4-thiazolylmethyl-[(1S)-1-[[[(1S,2R)-3-[(2S)-2-[[(1,1-dimethylethyl)amino]carbonyl]-4-[(4-fluorophenyl)methyl]-1-piperazinyl]-2-hydroxy-1-(phenylmethyl)propyl]amino]carbonyl]-2-methylpropyl]carbamate The title compound was prepared according to the method described in Example 15B, substituting 4-fluorobenzyl chloride in place of 3,4-dioxomethylenebenzyl chloride.

MS: 711 (M+H)+.

¹H NMR (CDCl₃) δ 0.68 (d, J=6.3 Hz, 3H), 0.84 (d, J=6.3 Hz, 3H), 1.35 (s, 9H), 2.06 (hextet, J=6.0 Hz, 1H), 2.28 (m, 1H), 2.47 (m, 1H), 2.55 (m, 1H), 2.59 (m, 2H), 2.71 (m, 2H), 2.73 (s, 3H), 2.76 (m, 1H), 2.83 (m, 2H), 2.90 (m, 1H), 3.35 (m, 1H), 3.43 (s, 2H), 3.80 (m, 1H), 3.86 (dd, J=7.5, 6.0 Hz, 1H), 4.22 (septet, J=4.5 Hz, 1H), 5.10 (m, 1H), 5.14 (s, 2H), 6.15 (d, J=7.5 Hz, 1H), 7.03 (t, J=8.4 Hz, 2H), 7.12–7.22 (m, 8H), 8.21 (br s, 1H).

EXAMPLE 18

2-Ethyl-4-thiazolylmethyl-(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate 18A. 2-Ethyl-4-thiazolylmethyl-(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl]carbamate The title compound was prepared according to the method of Example 1C, substituting [(2-ethyl-4-thiazolyl)methyloxycarbonyl]-L-valine in place of [(2-isopropyl-4-thiazolyl)methyloxycarbonyl]-L-valine. This was followed by treatment of the product with trifluoroacetic acid according to the method of Example 1D.

18B. 2-Ethyl-4-thiazolylmethyl-(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate The title compound was prepared by reacting 2-ethyl-4-thiazolylmethyl-(1S)-1-[[[(1S,2R)-3-[(2S)-4-[1,1-dimethylethyl-oxy(carbonyl)]-2-[[(1,1-dimethylethyl)amino]carbonyl]-1-piperazinyl]-2-hydroxy-1-(phenylmethyl)propyl]amino]carbonyl]-2-methylpropyl]carbamate, 98 mg (0.16 mmol), with 3,4-dimethoxybenzyl chloride, 30 mg (0.18 mmol), according to the method described in Example 15(B).

MS: 767 (M+H)+.

¹H NMR (CDCl₃) δ 0.67 (d, J=6.3 Hz, 3H), 0.84 (d, J=6.3 Hz, 3H), 1.36 (s, 9H), 1.40 (d, J=7.5, 6H), 2.05 (hextet, J=6.0 Hz, 1H), 2.23 (m, 1H), 2.48 (m, 1H), 2.58 (dd, J=12.0, 3.0 Hz, 2H), 2.71 (m, 2H), 2.83 (m, 1H), 2.90 (m, 1H), 3.05 (q, J=7.5 Hz, 2H), 3.31 (m, 1H), 3.35 (m, 1H), 3.40 (AB, J=15.0 Hz, 2H), 3.88 (s, 3H), 3.89 (s, 3H), 4.22 (m, 1H), 4.88 (m, 1H), 5.08 (m, 1H), 5.16 (s, 2H), 6.11 (d, J=7.5 Hz, 1H), 6.77 (s, 1H), 6.82 (s, 2H), 7.12–7.22 (m, 8H), 8.21 (br s, 1H).

EXAMPLE 19

2-(1-Methylethyl)-5-thiazolylmethyl-[(1S)-1-[[[(1S,2R)-3-[(2S)-4-[(3,4-dimethoxylphenyl)methyl]-2-[[[(1,1-dimethylethyl)amino]carbonyl]-1-piperazinyl]-2-hydroxy-1-(phenylmethyl)propyl]amino]carbonyl]-2-methylpropyl]carbamate 19A. 2-(1-Methylethyl)-5-thiazolylmethyl-[(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl]carbamate A solution of 1.5 g (3.3 mmol) of 1-[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amine in 7 ml of THF and 7 ml of methylene chloride was prepared and treated with 1.0 g (3.3 mmol) of [(2-isopropyl-5-thiazolyl)methyloxycarbonyl]-L-valine, 642 mg (3.3 mmol) of EDAC, 45 mg (0.33 mmol) of HOBT, and 466 μl (3.3 mmol) of triethyl amine. The solution was stirred at room temperature for 6 hours, and concentrated in vacuo. The residue was taken up with ethyl acetate, washed with equal portions (15 mL) of 3 N HCl solution, 10% aqueous NaHCO₃, and saturated brine, dried over MgSO₄, and concentrated in vacuo. The resulting mixture was purified by chromatography on silica gel, using 5% methanol:methylene chloride, to provide the title compound yield: 2.1 g, 88%).

MS: 731 (M+H)+.

¹H NMR (DMSO-d₆) δ 1.08 (d, J=7 Hz, 6H), 2.78 (heptet, J=7 Hz, 1H), 9.06 (br s, 1H), 9.30 (br s, 1H).

19B. 2-(1-Methylethyl)-5-thiazolylmethyl-[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate The title compound was prepared in two steps. First, 2-(1-methylethyl)-5-thiazolylmethyl-[(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl]

carbamate was treated with trifluoroacetic acid according to the method described in Example 1D. This was followed by akylation of the product according to the method of Example 1E, substituting 3,4-dimethylbenzyl chloride in place of 3,4-dioxomethylenebenzyl chloride.

MS: 781 (M+H)+.

$^1$H NMR (CDCl$_3$) δ0.72 (d, J=6.3 Hz, 3H), 0.86 (d, J=6.3 Hz, 3H), 1.37 (s, 9H), 1.40 (d, J=6.3, 6H), 2.01 (hextet, J=6.0 Hz, 1H), 2.22 (dt, J=7.5, 3.0 Hz, 1H), 2.43 (m, 1H), 2.55 (m, 2H), 2.73 (m, 3H), 2.88 (m, 2H), 2.93 (m, 1H), 3.30 (heptet, J=6.3 Hz, 1H), 3.38 (m, 1H), 3.41 (AB, J=15.0 Hz, 2H), 3.80 (m, 1H), 3.87 (s, 3H), 3.88 (s, 3H), 4.22 (septet, J=4.5 Hz, 1H), 5.07 (d, J=8.4 Hz, 1H), 5.20 (d, J=3.0 Hz, 2H), 6.06 (d, J=9.0 Hz, 1H), 6.76 (s, 1H), 6.82 (s, 2H), 7.12–7.22 (m, 7H), 7.61 (s, 1H), 8.28 (br s, 1H).

EXAMPLE 20

2-Ethyl-5-thiazolylmethyl-(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate 20A. 2-Ethyl-5-thiazolylmethyl-(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl] carbamate The title compound was prepared according to the method described in Example 19A, substituting [(2-ethyl-5-thiazolyl)methyloxycarbonyl]-L-valine in place of [(2-isopropyl-5-thiazolyl)methyloxycarbonyl]-L-valine.

20B. 2-Ethyl-5-thiazolylmethyl-(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2carbamate The title compound was prepared in two steps. First, 2-ethyl-5-thiazolylmethyl-(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl] carbamate was treated with trifluoroacetic acid according to the method described in Example 1D. This was followed by akylation of the product according to the method of Example 1E, substituting 3,4-dimethylbenzyl chloride in place of 3,4-dioxomethylenebenzyl chloride.

MS: 767 (M+H)+.

$^1$H NMR (CDCl$_3$) δ0.73 (d, J=6.3 Hz, 3H), 0.86 (d, J=6.3 Hz, 3H), 1.37 (s, 9H), 1.38 (t, J=7.5, 3H), 2.02 (m, 1H), 2.23 (dt, J=7.5, 3.0 Hz, 1H), 2.45 (m, 1H), 2.56 (m, 2H), 2.72 (m, 2H), 2.77 (m, 1H), 2.89 (m, 2H), 3.02 (q, J=7.5 Hz, 2H), 3.39 (t, J=3.3 Hz, 1H), 3.41 (AB, J=15.0 Hz, 2H), 3.81 (m, 2H), 3.88 (s, 3H), 3.89 (s, 3H), 4.21 (m, 1H), 5.06 (d, J=9.0 Hz, 1H), 5.20 (d, J=5.4 Hz, 2H), 6.06 (d, J=9.0 Hz, 1H), 6.76 (s, 1H), 6.82 (s, 2H), 7.13–7.23 (m, 7H), 7.61 (s, 1H), 8.27 (br s, 1H).

EXAMPLE 21

2-Methyl-5-thiazolylmethyl-[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl]carbamate 21A. 2-Methyl-5-thiazolylmethyl-[(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl] carbamate The title compound was prepared according to the method described in Example 19A, substituting [(2-methyl-5-thiazolyl)methyloxycarbonyl]-L-valine in place of [(2-isopropyl-5-thiazolyl)methyloxycarbonyl]-L-valine.

21B. 2-Methyl-5-thiazolylmethyl-[(1S)-1-[[[(1S,2R)-3-[(2S)-4-[(3,4-dimethoxylphenyl)methyl]-2-[[(1,1-dimethylethyl)amino]carbonyl]-1-piperazinyl]-2-hydroxy-1-(phenylmethyl)propyl]amino]carbonyl]-2-methylpropyl] carbamate The title compound was prepared in two steps. First, 2-methyl-5-thiazolylmethyl-[(1S)-1-[[[(1S,2R)-3-[(2S)-4-[1,1-dimethylethyloxy(carbonyl)]-2-[[(1,1-dimethylethyl)amino]carbonyl]-1-piperazinyl]-2-hydroxy-1-(phenylmethyl)propyl]amino]carbonyl]-2-methylpropyl] carbamate was treated with trifluoroacetic acid according to the method described in Example 1D. This was followed by akylation of the product according to the method of Example 1E, substituting 3,4-dimethylbenzyl chloride in place of 3,4-dioxomethylenebenzyl chloride.

MS: 753 (M+H)+.

$^1$H NMR (CDCl$_3$) δ0.72 (d, J=6.3 Hz, 3H), 0.86 (d, J=6.3 Hz, 3H), 1.46 (s, 9H), 2.01 (hextet, J=6.0 Hz, 1H), 2.22 (dt, J=7.5, 3.0 Hz, 1H), 2.43 (dd, J=12.0, 3.0 Hz, 1H), 2.56 (m, 2H), 2.69 (s, 3H), 2.72 (m, 1H), 2.77 (m, 1H), 2.86 (m, 2H), 2.92 (m, 1H), 3.39 (t, J=3.0 Hz, 1H), 3.41 (AB, J=15.0 Hz, 2H), 3.80 (m, 2H), 3.87 (s, 3H), 3.88 (s, 3H), 4.21 (septet, J=4.5 Hz, 1H), 5.06 (d, J=9.0 Hz, 1H), 5.19 (AB, J=9.6 Hz, 2H), 6.07 (d, J=9.0 Hz, 1H), 6.75 (s, 1H), 6.82 (s, 2H), 7.12–7.22 (m, 7H), 7.58 (s, 1H), 8.27 (br s, 1H).

EXAMPLE 22

N'-[(1R)-1-[[[(1S,2R)-3-[(2S)-2-[[(1,1-Dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-(5-thiazolylmethyl)urea 22A. N'-[(1R)-1-[[[(1S,2R)-3-[(2S)-2-[[(1,1-Dimethylethyl)amino]carbonyl]-4-[1,1-dimethylethyloxy(carbonyl)]-1-piperazinyl]-2-hydroxy-1-(phenylmethyl)propyl]amino]carbonyl]-2-methylpropyl]-N-methyl-N-(5-thiazolylmethyl)urea The title compound was prepared according to the method described in Example 19A, substituting [N-methyl-(5-thiazolyl)methylaminocarbonyl]-D-valine in place of [(2-isopropyl-5-thiazolyl)methyloxycarbonyl]-L-valine.

22B. N'-[(1R)-1-[[[(1S,2R)-3-[(2S)-2-[[(1,1-Dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-(5-thiazolylmethyl)urea The title compound was prepared in two steps. N'-[(1R)-1-[[[(1S,2R)-3-[(2S)-2-[[(1,1-dimethylethyl)amino] carbonyl]-4-[1,1-dimethylethyloxy(carbonyl)]-1-piperazinyl]-2-hydroxy-1-(phenylmethyl)propyl]amino] carbonyl]-2-methylpropyl]-N-methyl-N-(5-thiazolylmethyl)urea was treated with trifluoroacetic acid according to the method described in Example 1D. This was followed by akylation of the product according to the method of Example 1E, substituting 5-thiazolyl chloride in place of 3,4-dioxomethylenebenzyl chloride.

MS: 699 (M+H)+.

$^1$H NMR (CDCl$_3$)δ0.58 (d, J=6.3 Hz, 3H), 0.66 (d, J=6.3 Hz, 3H), 1.38 (s, 9H), 1.75 (m, 1H), 2.35 (m, 1H), 2.60 (m, 2H), 2.70 (m, 2H), 2.85 (m, 2H), 2.86 (s, 3H), 2.92 (m, 3H), 3.30 (t, J=3.3 Hz, 1H), 3.74 (s, 2H), 3.88 (m, 1H), 3.97 (dd, J=8.4, 6.0 Hz, 1H), 4.28 (m, 2H), 4.53 (br s, 1H), 4.65 (d, J=3.3 Hz, 2H), 5.03 (d, J=7.5, 1H), 6.09 (d, J=9.0 Hz, 1H), 7.17–7.27 (m, 5H), 7.73 (s, 2H), 8.73 (s, 1H), 8.80 (s, 1H).

EXAMPLE 23

N'-[(1S)-1-[[[(1S,2R)-3-[(2S)-2-[[(1,1-Dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-(5-thiazolylmethyl)urea 23A. N'-[(1S)-1-[[[(1S,2R)-3-[(2S)-2-[[(1,1-Dimethylethyl)amino]carbonyl]-4-[1,1-dimethylethyloxy(carbonyl)]-1-piperazinyl]-2-hydroxy-1-(phenylmethyl)propyl]amino]carbonyl]-2-methylpropyl]-N-methyl-N-(5-thiazolylmethyl)urea The title compound was prepared according to the method described in Example 19A, substituting [N-methyl-(5-thiazolyl)methylaminocarbonyl]-L-valine in place of [(2-isopropyl-5-thiazolyl)methyloxycarbonyl]-L-valine.

23B. N'-[(1S)-1-[[[(1S,2R)-3-[(2S)-2-[[(1,1-Dimethylethyl)amino]carbonyl]-4-(5-thiazolylmethyl)-1-piperazinyl]-2-hydroxy-1-(phenylmethyl)propyl]amino]carbonyl]-2-methylpropyl]-N-methyl-N-(5-thiazolylmethyl)urea The title compound was prepared in two steps. First, N'-[(1S)-1-[[[(1S,2R)-3-[(2S)-2-[[(1,1-dimethylethyl)amino]carbonyl]-4-[1,1-dimethylethyloxy(carbonyl)]-1-piperazinyl]-2-hydroxy-1-(phenylmethyl)propyl]amino]carbonyl]-2-methylpropyl]-N-methyl-N-(5-thiazolylmethyl)urea was treated with trifluoroacetic acid according to the method described in Example 1D. This was followed by akylation of the product according to the method of Example 1E, substituting 5-thiazolyl chloride in place of 3,4-dioxomethylenebenzyl chloride.

MS: 699 (M+H)$^+$.

$^1$H NMR (CDCl$_3$) δ0.78 (d, J=6.3 Hz, 3H), 0.87 (d, J=6.3 Hz, 3H), 1.49 (s, 9H), 2.02 (m, 1H), 2.33 (m, 2H), 2.57 (m, 2H), 2.75 (m, 2H), 2.82 (s, 3H) 2.89 (m, 3H), 3.38 (t, J=3.0 Hz, 1H), 3.73 (d, J=3.3 Hz, 2H), 3.79 (m, 1H), 4.03 (dd, J=8.4, 6.3 Hz, 1H), 4.20 (m, 1H), 4.66 (AB, J=15 Hz, 2H), 4.78 (m, 1H), 4.81 (d, J=8.4 Hz, 2H), 6.11 (d, J=9.0 Hz, 1H), 7.11–7.23 (m, 5H), 7.73 (s, 1H), 7.76 (s, 1H), 7.82 (br s, 1H), 8.75 (s, 1H), 8.80 (s, 1H).

EXAMPLE 24

5-Thiazolylmethyl-[(1S)-1-[[[(1S,2R)-3-[(2S)-2-[[(1,1-dimethylethyl)amino]carbonyl]-4-(phenylmethyl)-1-piperazinyl]-2-hydroxy-1-(phenylmethyl)propyl]amino]carbonyl]-2-methylpropyl]carbamate 24A. 5-Thiazolylmethyl-[(1S)-1-[[[(1S,2R)-3-[(2S)-2-[[(1,1-dimethlethyl)amino]carbonyl]-4-[1,1-dimethylethyloxy(carbonyl)]-1-piperazinyl]-2-hydroxy-1-(phenylmethyl)propyl]amino]carbonyl]-2-methylpropyl]carbamate The title compound was prepared according to the method described in Example 19A, substituting [(5-thiazolyl)methyloxycarbonyl]-L-valine, in place of [(2-isopropyl-5-thiazolyl)methyloxycarbonyl]-L-valine.

24B. 5-Thiazolylmethyl-[(1S)-1-[[[(1S,2R)-3-[(2S)-2-[[(1,1-dimethylethyl)amino]carbonyl]-4-(phenylmethyl)-1-piperazinyl]-2-hydroxy-1-(phenylmethyl)propyl]amino]carbonyl]-2-methylpropyl]carbamate The title compound was prepared in two steps. First, 5-thiazolylmethyl-[(1S)-1-[[[(1S,2R)-3-[(2S)-2-[[(1,1-dimethylethyl)amino]carbonyl]-4-[1,1-dimethylethyloxy(carbonyl)]-1-piperazinyl]-2-hydroxy-1-(phenylmethyl)propyl]amino]carbonyl]-2-methylpropyl]carbamate was treated with trifluoroacetic acid according to the method described in Example 1D. This was followed by akylation of the product according to the method of Example 1E, substituting benzyl bromide in place of 3,4-dioxomethylenebenzyl chloride.

MS: 699 (M+H)$^+$.

$^1$H NMR (CDCl$_3$) δ0.78 (d, J=6.3 Hz, 3H), 0.87 (d, J=6.3 Hz, 3H), 1.49 (s, 9H), 2.02 (m, 1H), 2.33 (m, 2H), 2.57 (m, 2H), 2.75 (m, 2H), 2.82 (s, 3H) 2.89 (m, 3H), 3.38 (t, J=3.0 Hz, 1H), 3.73 (d, J=3.3 Hz, 2H), 3.79 (m, 1H), 4.03 (dd, J=8.4, 6.3 Hz, 1H), 4.20 (m, 1H), 4.66 (AB, J=15 Hz, 2H), 4.78 (m, 1H), 4.81 (d, J=8.4 Hz, 2H), 6.11 (d, J=9.0 Hz, 1H), 7.11–7.23 (m, 5H), 7.73 (s, 1H), 7.76 (s, 1H), 7.82 (br s, 1H), 8.75 (s, 1H), 8.80 (s, 1H).

EXAMPLE 25

5-Thiazolylmethyl-(1S)-1-[[[(1S,2R)-3-[(2S)-2-[[(1,1-dimethylethyl)amino]carbonyl]-4-(5-thiazolylmethyl)-1-piperazinyl]-2-hydroxy-1-(phenylmethyl)propyl]amino]carbonyl]-2-methylpropyl]carbamate The title compound was prepared according to the method described in Example 24B, by akylation of 5-thiazolylmethyl-[(1S)-1-[[[(1S,2R)-3-[(2S)-2-[[(1,1-dimethylethyl)amino]carbonyl]-1-piperazinyl]-2-hydroxy-1-(phenylmethyl)propyl]amino]carbonyl]-2-methylpropyl]carbamate with 5-thiazolyl methyl chloride in place of benzyl bromide.

MS: 686 (M+H)$^+$.

$^1$H NMR (CDCl$_3$) δ0.62 (d, J=6.3 Hz, 3H), 0.86 (d, J=6.3 Hz, 3H), 1.39 (s, 9H), 2.01 (m, 1H), 2.30 (m, 1H), 2.52 (m, 1H), 2.67 (m, 2H), 2.71 (m, 1H), 2.75 (m, 2H), 2.87 (m, 2H), 2.92 (m, 1H), 3.29 (t, J=3.0 Hz, 1H), 3.74 (d, J=4.4 Hz, 2H), 4.80 (m, 2H), 4.85 (m, 1H), 4.21 (m, 1H), 5.08 (t, J=9.0 Hz, 1H), 5.18 (d, J=4.5 Hz, 1H), 6.07 (d, J=9.6 Hz, 2H), 7.11–7.24 (m, 5H), 7.74 (s, 1H), 7.88 (s, 1H), 8.80 (s, 1H), 8.81 (s, 1H).

EXAMPLE 26

N'-[(1S)-1-[[[(1S,2R)-3-[[[(1,1-Dimethylethyl)amino]carbonyl](2-methylethyl)propylamino]-2-hydroxy-1-(phenylmethyl)propyl]amino]carbonyl]-2-methylpropyl]-N-methyl-N-[2-(1-methylethyl)-4-thiazolylmethyl]urea The title compound was prepared according to the method described in Example 12A, by coupling N-methyl-N-[(((2-isopropyl-4-thiazolyl)methyl)amino)-carbonyl]-L-valine with N-(3S-amino-2R-hydroxy-4-phenylbutyl)-N-(2-methylpropyl)-N'-(1,1-dimethylethyl)urea, prepared according to the method described in J. Med. Chem., 1993, 36, 288–291.

Elemental analysis:

Theory: C: 62.34, H: 8.44, N: 13.64.

Found: C: 59.60, H: 7.37, N: 12.86.

EXAMPLE 27

2-(1-Methylethyl)-4-thiazolylmethyl-[(1S)-1-[[[(1S,2R)-3-[[[(1,1-dimethylethyl)amino]carbonyl](2-methylethyl)propylamino]-2-hydroxy-1-(phenylmethyl)propyl]amino]carbonyl]-2-methylpropyl]carbamate The title compound was prepared according to the method described in Example 26, by coupling N-[(2-isopropyl-4-thiazolyl)methyloxycarbonyl]-L-valine with N-(3S-amino-2R-hydroxy-4-phenylbutyl)-N-(2-methylpropyl)-N'-(1,1-dimethylethyl)urea, prepared according to the method described in J. Med. Chem., 1993, 36, 288–291.

Elemental analysis:
Theory: C: 61.69, H: 8.13, N: 11.61.
Found: C: 60.80, H: 8.21, N: 11.18.

EXAMPLE 28

2-(1-Methylethyl)-4-thiazolylmethyl-(1S)-1-[[[(1S, 2R)-3-[[(4-aminophenyl)sulfonyl](1-methylethyl)amino]-2-hydroxy-1-(phenylmethyl)propyl]amino]carbonyl]-2-methylpropyl]carbamate The title compound was prepared in two steps. First, N-isobutyl-2(R)-hydroxy-3(S)-amino-4-phenyl-(4'-nitrophenyl)sulfonamide, prepared according to the method described in *J. Am. Chem. Soc.*, 1995, 117, 1181–1182, was coupled with [(2-isopropyl-4-thiazolyl)methyloxycarbonyl]-L-valine according to the method described in Example 1C. This was followed by hydrogenation of the product over Pd/C under 1 atmosphere of hydrogen. The catalyst was removed via filtration over a celite pad and the solvent was evaporated at reduced pressure to provide the title compound as a white foam.

MS: 674 (M+H)$^+$.

$^1$H NMR (DMSO-d$_6$) δ0.65 (d, J=6.3 Hz, 3H), 0.67 (d, J=6.3 Hz, 3H), 0.77 (d, J=6.0 HZ, 3H), 0.81 (t, J=6.0 HZ, 3H), 1.32 (d, J=6.3 Hz, 6H), 1.77 (m, 1H), 1.90 (m, 1H), 2.60 (m, 2H), 2.65 (m, 1H), 2.72 (m, 1H), 2.83 (d, J=7.5 Hz, 1H), 2.89 (d, J=9.0 Hz, 1H), 3.00 (m, 2H), 3.25 (m, 1H), 3.61 (m, 1H), 3.75 (dd, J=9.0, 6.3 Hz, 1H), 3.94 (m, 1H), 4.96 (d, J=6.3 Hz, 1H), 5.02 (s, 2H), 5.98 (s, 2H), 6.60 (t, J=9.0 Hz, 2H), 7.10 (m, 2H), 7.15–7.22 (m, 3H), 7.39 (d, J=8.4 Hz, 2H), 7.43 (s, 1H), 7.72 (d, J=9.0 Hz, 1H).

EXAMPLE 29

N'-[(1S)-1-[[[(1S,2R)-3-[[(4-Aminophenyl)sulfonyl](1-methylethyl)amino]-2-hydroxy-1-(phenylmethyl)propyl]amino]carbonyl]-2-methylpropyl]-N-methyl-N-[2-(1-methylethyl)-4-thiazolylmethyl]urea The title compound was prepared in two steps. First, N-isopropyl-2(R)-hydroxy-3(S)-amino-4-phenyl-(4'-nitrophenyl)sulfonamide was coupled with N-methyl-N-[(((2-isopropyl-4-thiazolyl)methyl)amino)carbonyl]-L-valine according to the method described in Example 12A. This was followed by hydrogenation of the product over Pd/C under 1 atmosphere of hydrogen. The catalyst was removed via filtration over a celite pad and the solvent was evaporated at reduced pressure to provide the title compound as a white foam.

MS: 674 (M+H)$^+$.
Elemental analysis:
Theory: C: 58.93, H: 7.14, N: 12.50.
Found: C: 58.30, H: 7.28, N: 12.11.

EXAMPLE 30

2-(1-Methylethyl)-5-thiazolylmethyl-[(1S)-1-[[[(1S, 2R)-3-[(3S)-3-[[(1,1-dimethylethyl)amino]carbonyl](4aα,8aα)octahydro-2-isoquinolinyl]-2-hydroxy-1-(phenylmethyl)propyl]amino]carbonyl]-2-methylpropyl]carbamate The title compound was prepared according to the method described in Example 1C, by coupling 2-(3(S)-amino-2(R)-hydroxy-4-phenylbutyl)-N-tert-butyldecahydro-(4aS,8aS)-isoquinoline-3(S)-carboxamide with [(2-isopropyl-4-thiazolyl)methyloxycarbonyl]-L-valine, prepared according to the method described in *J. Org. Chem.*, 1994, 59, 3656–3664.

Elemental analysis:
Theory: C: 65.01, H: 8.35, N: 10.25.
Found: C: 63.70, H: 8.19, N: 10.05.

EXAMPLE 31

N'-[(1S)-1-[[[(1S,2R)-3-[(3S)-3-[[(1,1-Dimethylethyl)amino]carbonyl](4aα,8aα)octahydro-2-isoquinolinyl]-2-hydroxy-1-(phenylmethyl)propyl]amino]carbonyl]-2-methylpropyl]-N-methyl-N-[2-(1-methylethyl)-5-thiazolylmethyl]urea The title compound was synthesized according to the method described in Example 12A by coupling of 2-(3(S)-amino-2(R)-hydroxy-4-phenylbutyl)-N-tert-butyldecahydro-(4aS,8aS)-isoquinoline-3(S)-carboxamide with N-methyl-N-[(((2-isopropyl-4-thiazolyl)methyl)amino)carbonyl]-L-valine which was prepared according to the method described in *J. Org Chem.*, 1994, 59, 3656–3664.

Elemental analysis:
Theory: C: 65.52, H: 8.62, N: 12.07.
Found: C: 64.50, H: 8.72, N: 12.09.

EXAMPLE 32

N'-[(1S)-1-[[[(1S,2R)-3-[(2S,4R)-2-[[(1,1-Dimethylethyl)amino]carbonyl]-4-(5-thiazolylmethoxy)-1-piperidinyl]-2-hydroxy-1-(phenylmethyl)propyl]amino]carbonyl]-2-methylpropyl]-N-methyl-N-[2-(1-methylethyl)-4-thiazolylmethyl]urea 32A. 1-cis-N-(1,1-Dimethylethyl)-1-(1,1-dimethylethyloxycarbonyl)-4-(5-thiazolylmethyloxy)piperidine-2-carboxamide 1-cis-N-(1,1-Dimethylethyl)-1-(1,1-dimethylethyloxycarbonyl)-4-hydroxypiperidine-2-carboxamide was prepared according to the methods described in EP 560 268 A1. The hydroxy-carboxamide compound was treated with sodium hydride and 5-thiazolyl methyl chloride in DMF at 0° C. to provide the title compound.

32B. 1-cis N-(1,1-Dimethylethyl)-4-(5-thioazoylmethyloxy)piperidine-2-carboxamide A solution of 1.24 g of 1-cis-N-(1,1-dimethylethyl)-1-(1, 1-dimethylethyloxycarbonyl)-4-(5-thiazolylmethyloxy)piperidine-2-carboxamide in 10 ml of THF was prepared. The mixture was treated with 3 N HCl, and stirred at room temperature for 1 hour. After stirring, the reaction was it was partitioned between methylene chloride and saturated sodium bicarbonate. The organic layer was washed with brine, dried with Na2SO$_4$ and evaporated to dryness to provide 836 mg of desired product.

32C. N'-[(1S)-1-[[[(1S,2R)-3-[(2S,4R)-2-[[(1,1-Dimethylethyl)amino]carbonyl]-4-(5-thiazolylmethoxy)-1-piperidinyl]-2-hydroxy-1-(phenylmethyl)propyl]amine The title compound was synthesized in two steps. N'-[(1S)-1-[[[(1S,2R)-3-[(2S,4R)-2-[[(1,1-Dimethylethyl)amino]carbonyl]-4-(5-thiazolylmethoxy)-1-piperidinyl]-2-hydroxy-1-(phenylmethyl)propyl]amine was prepared according to the method described in Example 1A by using t-butyloxycarbonyl phenylalanylepoxide replacing N-benzyloxycarbonyl phenylalanylepoxide followed by column purification. The resulting product was treated with trifluoroacetic acid (TFA) in methylene chloride at room temperature.

32D. N'-[(1S)-1-[[[(1S,2R)-3-[(2S,4R)-2-[[(1,1-Dimethylethyl)amino]carbonyl]-4-(5-thiazolylmethoxy)-1- piperidinyl]-2-hydroxy-1-(phenylmethyl)propyl]amino]carbonyl]-2-methylpropyl]-N-methyl-N-[2-(1-methylethyl)-4-thiazolylmethyl]urea The title compound was synthesized by the method described in Example 12A using N'-[(1S)-1-[[[(1S,2R)-3-[(2S,4R)-2-[[(1,1-dimetylethyl)amino]carbonyl]-4-(5-thiazolylmethoxy)-1-piperidinyl]-2-hydroxy-1-(phenylmethyl)propyl]amine and N-methyl-N-[(((2-isopropyl-4-thiazolyl)methyl)amino)carbonyl]-L-valine.

MS: 756 (M+H)$^+$.

$^1$H NMR (CDCl$_3$) δ0.65 (d, J=6.3 Hz, 3H), 0.92 (d, J=6.3 Hz, 3H), 1.32 (d, J=3.0 HZ, 3H), 1.34 (d, J=3.0 Hz, 2H), 1.35 (s, 9H), 1.53 (m, 1H), 1.58 (m, 1H), 1.91 (m, 1H), 2.20–2.37 (m, 4H), 2.67 (m, 1H), 2.69 (m, 1H), 2.80 (dd, J=11.4, 3.0 Hz, 1H), 2.87 (dd, J=15.0, 3.3 Hz, 1H), 2.97 (s, 3H), 3.21 (heptet, J=6.3 Hz, 1H), 3.40 (t, J=4.5 Hz, 1H), 3.44 (m, 1H), 3.91 (t, J=5.7 Hz, 1H), 4.03 (m, 2H), 4.12 (m, 1H), 4.35 (AB, J=15.0 Hz, 2H), 4.78 (AB, J=12.0 Hz, 2H), 6.48 (d, J=8.1 Hz, 1H), 6.61 (s, 1H), 7.00 (s, 1H), 7.09–7.18 (m, 6H), 7.78 (s, 1H), 8.79 (s, 1H).

EXAMPLE 33

2-(1-Methylethyl)-4-thiazolylmethyl[(1S)-1-[[[(1S,2R)-3-[(2S,4R)-2-[[(1,1-dimethylethyl)amino]carbonyl]-4-(5-thiazolylmethoxy)-1-piperidinyl]-2-hydroxy-1-(phenylmethyl)propyl]amino]carbonyl]-2-methylpropyl]carbamate The title compound is prepared according to the procedure described in example 32C using N-[(2-isopropyl-4-thiazolyl)methyloxycarbonyl]-L-valine in place of N-methyl-N-[(((2-isopropyl-4-thiazolyl)methyl)amino)carbonyl]-L-valine as a coupling reagent.

EXAMPLE 34

S-[2-(1-Methylethyl)-4-thiazolylmethyl][(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamothioate 34A. 2-Isopropyl-4-(methanesulfonyloxymethyl)thiazole A solution of 1.2 mmol of 4-(hydroxymethyl)-2-isopropylthiazole and 1.3 mmol of diisopropylethylamine in 20 ml of dichloromethane is cooled to –20° C. and treated dropwise with 1.3 mmol of methanesulfonyl chloride. The resulting mixture is stirred for 1 hour, quenched with aqueous citric acid, separated, dried over Na$_2$SO$_4$, and concentrated in vacuo to provide the title compound.

34B. 2-Isopropyl-4-(mercaptomethyl)thiazole

A mixture of 0.8 mmol of the product prepared in Example 34A and 1.0 mmol of sodium hydrosulfide hydrate in 20 ml of THF is heated at reflux until analysis by thin layer chromatography indicates consumption of the starting material. The resulting mixture is allowed to cool, concentrated in vacuo, partitioned between dichloromethane and water, dried over Na$_2$SO$_4$, and concentrated to provide the crude compound.

34C. N-((2-Isopropyl-4-thiazolyl)thiomethoxycarbonyl) valine methyl ester

A solution of 2.18 g (15 mmol) of 2-Isopropyl-4-(mercaptomethyl)thiazole, 15.8 mmol of α-isocyanatovaline methyl ester and 1.5 mmol of 4-dimethylaminopyridine in 75 ml of dichloromethane is heated at reflux for about 5 hours. The resulting solution is washed successively with 10% citric acid, aqueous NaHCO$_3$ and brine, dried over Na$_2$SO$_4$, and concentrated in vacuo.

Silica gel chromatography of the residue using 5% ethyl acetate in chloroform will provide the title compound.

34D. N-((2-Isopropyl-4-thiazolyl)thiomethoxycarbonyl) valine

A solution of product, prepared in Example 34C in dioxane is treated with 0.50 M aqueous LiOH. The resulting solution is stirred at ambient temperature for about 30 minutes, treated with 1 M HCl, and concentrated in vacuo. The residue is taken up in dichloromethane, washed with water, dried over Na$_2$SO$_4$, and concentrated in vacuo to provide the title compound.

34E. S-[2-(1-Methylethyl)-4-thiazolylmethyl[(1S)-1-[[[(1S,2R)-3-[(2S)-2-[[(1,1-dimethylethyl)amino]carbonyl-4-[[(1,1-dimethylethyl)carbonyl]oxy]-1-piperazinyl]-2-hydroxy-1-(phenylmethyl)propyl]amino]carbonyl]-2-methylpropyl]carbamothioate The title compound is prepared according to the method described in Example 1C, substituting N-((2-Isopropyl-4-thiazolyl)thiomethoxycarbonyl)valine in place of [(2-isopropyl-4-thiazolyl)methyloxycarbonyl]-L-valine.

34F. S-[2-(1-Methylethyl)-4-thiazolylmethyl[(1S)-1-[[[(1S,2R)-3-[(2S)-2-[[(1,1-dimethylethyl)amino]carbonyl]-1-piperazinyl]-2-hydroxy-1-(phenylmethyl)propyl]amino]carbonyl]-2-methylpropyl]carbamothioate The title compound is prepared according to the method described in Example 1D, substituting S-[2-(1-methylethyl)-4-thiazolylmethyl][(1S)-1-[[[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl]carbamothioate in place of 2-(1-methylethyl)-4-thiazolylmethyl-(1S)-1-[[[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl]carbamate.

34G. S-[2-(1-Methylethyl)-4-thiazolylmethyl][(1S)-1-[[[(1S,2R)-3-[(2S)-4-(1,3-benzodioxol-5-ylmethyl)-2-[[(1,1-dimethylethyl)amino]carbonyl]-1-piperazinyl]-2-hydroxy-1-(phenylmethyl)propyl]amino]carbonyl]-2-methylpropyl]carbamothioate The title compound is prepared according to the method described in Example 1E, substituting S-[2-(1-methylethyl)-4-thiazolylmethyl][(1S)-1-[[[(1S,2R)-3-[(2S)-2-[[(1,1-dimethylethyl)amino]carbonyl]-1-piperazinyl]-2hydroxy-1-(phenylmethyl)propyl]amino]carbonyl]-2-methylpropyl]carbamothioate in place of 2-(1-methylethyl)-4-thiazolylmethyl-(1S)-1-[[[(1S,2R)-3-[(2S)-2-[[(1,1-dimethylethyl)amino]carbonyl]-1-piperazinyl]-2-hydroxy-1-(phenylmethyl)propyl]amino]carbonyl]-2-methylpropyl]carbamate.

EXAMPLE 35

4-(1,3-Benzodioxol-5-ylmethyl)-N-(1,1-dimethylethyl)-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide 35A. 2-Isopropylthiazole-4-carboxaldehyde A solution of 3.1 g (15.6 mmol) of ethyl 2-isopropylthiazole-4-carboxylate in 50 ml of dichloromethane was cooled under N$_2$ atmosphere to –78° C. and treated dropwise with 15.6 ml (23.4 mmol) of a 1.5 M solution of diisobutylaluminum hydride in toluene over a period of 1.5 h. After being stirred for an additional 0.5 h, the solution was quenched with 5 ml of methanol followed by 15 ml of aqueous Rochelle's salt. The resulting mixture was partitioned between chloroform and aqueous Rochelle's salt, dried over Na$_2$SO$_4$, and concentrated to provide 1.37 g (56%) of the crude desired compound, R$_f$ 0.47 (20% ethyl acetate in hexane).

$^1$H NMR (CDCl$_3$) d 1.45 (d, J=7 Hz, 6H), 3.39 (heptet, J=7 Hz, 1H), 8.07 (s, 1H), 10.00 (s, 1H).

Mass spectrum: (M+H)$^+$=156.

35B. (E)-Ethyl 3-(2-Isopropyl-4-thiazolyl)propenoate

A slurry of 60% NaH (18 mmol) in mineral oil was washed with hexane, decanted under N$_2$ atmosphere, and diluted with 25 ml of THF. The resulting mixture was cooled to 0° C., treated portionwise with 3.24 ml (16.4 mmol) of triethylphosphonoacetate. After addition, the solution was stirred for 10 minutes, treated with 1.37 g (8.84 mmol) of 2-isopropylthiazole-4-carboxaldehyde in 25 ml of THF, allowed to warm to ambient temperature for 25 minutes, and quenched with 100 ml of saturated aqueous NH$_4$Cl. The mixture was extracted with three 100 ml portions of ethyl acetate, dried over Na$_2$SO$_4$, and concentrated in vacuo. Silica gel chromatography of the residue using 5–10% ethyl acetate in hexane provided 1.61 g (81%) of the desired compound, R$_f$ 0.64 (20% ethyl acetate in hexane).

$^1$H NMR (CDCl$_3$) d 1.33 (t, J=7 Hz, 3H), 1.42 (d, J=7 Hz, 6H), 3.32 (heptet, J=7 Hz, 1H), 4.26 (q, J=7 Hz, 2H), 6.75 (d, J=15 Hz, 1H), 7.29 (s, 1H), 7.57 (d, J=15 Hz, 1H).

35C. Methyl 3-(2-Isopropyl-4-thiazolyl)propanoate

A solution of 225 mg (1 mmol) of (E)-ethyl 3-(2-isopropyl-4-thiazolyl)propenoate in 10 ml of freshly distilled (from calcium hydride) methanol and 1 ml of dry THF is treated with 49 mg (2 mmol) of magnesium turnings. The mixture is stirred for 20 minutes, and the magnesium is consumed. The resulting solution is poured over cold aqueous HCl, basified to pH 8 with NaHCO$_3$, extracted with ethyl acetate, dried over Na$_2$SO$_4$, and concentrated. Silica gel chromatography using 10% ethyl acetate in hexane provides a mixture of the desired compound and methyl 3-(2-isopropyl-4-thiazolinyl)propanoate.

35D. 3-(2-Isopropyl-4-thiazolyl)propanoic Acid

A solution of product, prepared in Example 35C in dioxane is treated with 0.50 M aqueous LiOH. The resulting solution is stirred at ambient temperature for about 30 minutes, treated with 8.7 ml of 1 M HCl, and concentrated in vacuo. The residue is taken up in dichloromethane, washed with water, dried over Na$_2$SO$_4$, and concentrated in vacuo to provide the title compound.

35E. N-(1,1-Dimethylethyl)-4-[[(1,1-dimethylethyl) carbonyl]oxy]-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide A solution of 3-(2-isopropyl-4-thiazolyl)propanoic acid, 1.1 equivalents of α-isocyanato-valine methyl ester and 4-dimethylaminopyridine (catalytic) in of dichloromethane is heated at reflux for about 5 hours. The resulting solution is washed successively with 10% citric acid, aqueous NaHCO$_3$ and brine, dried over Na$_2$SO$_4$, and concentrated in vacuo. Silica gel chromatography of the residue using 5% ethyl acetate in chloroform to provide the title compound.

35F. N-(1,1-Dimethylethyl)-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide The title compound is prepared according to the method described in Example 1C, substituting N-((2-Isopropyl-4-thiazolyl)propionyl)valine in place of [(2-isopropyl-4-thiazolyl)methyloxycarbonyl]-L-valine.

35G. N-(1,1-Dimethylethyl)-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide The title compound is prepared according to the method described in Example 1D, substituting 4-(1,1-dimethylethyloxy(carbonyl))-N-(1,1-dimethylethyl)-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide in place of 2-(1-methylethyl)-4-thiazolylmethyl-(1S)-1-[[[(1S,2R)-3-[(2S)-4-(1,1-dimethylethyloxy(carbonyl))-2-[[(1,1-dimethylethyl)amino]carbonyl]-1-piperazinyl]-2-hydroxy-1-(phenylmethyl)propyl]amino]carbonyl]-2-methylpropyl]carbamate.

35H. 4-(1,3-Benzodioxol-5-ylmethyl)-N-(1,1-dimethylethyl)-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide The title compound is prepared according to the method described in Example 1E, substituting N-(1,1-dimethylethyl)-1-[(2R,3S)-3-[[(2S)-2-[[3-[2-(1-methylethyl)-4-thiazolyl]-1-oxopropyl]amino]-3-methyl-1-oxobutyl]amino]-2-hydroxy-4-phenylbutyl]-2-piperazinecarboxamide in place of 2-(1-methylethyl)-4-thiazolylmethyl-(1S)-1-[[[(1S,2R)-3-[(2S)-2-[[(1,1-dimethylethyl)amino]carbonyl]-1-piperazinyl]-2-hydroxy-1-(phenylmethyl)propyl]amino]carbonyl]-2-methylpropyl]carbamate.

Fluorogenic Assay for Screening Inhibitors of HIV Protease

The inhibitory potency of the compounds of the invention can be determined by the following method:

A compound of the invention is dissolved in DMSO. A small aliquot is diluted with DMSO to 100 times the final concentration desired for testing. The test is carried out in a 6×50 mm tube in a total volume of 300 microliters. The final concentrations of the components in the reaction buffer are: 125 mM sodium acetate, 1 M sodium chloride, 5 mM dithiothreitol, 0.5 mg/ml bovine serum albumin, 1.3 $\mu$M fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100×(1−(rate in presence of inhibitor)/(rate in absence of inhibitor)).

Fluorogenic substrate: Dabcyl-Ser-Gln-Asn-Tyr-Pro-Ile-Val-Gln-EDANS wherein DABCYL=4-(4-dimethylaminophenyl)azobenzoic acid and EDANS=5-((2-aminoethyl)amino)naphthalene-1-sulfonic acid. All compounds tested at 1.0 nM were found to have an IC$_{50}$ of 100%. The test compounds were then tested at a concentration of 0.5 nM. The results are reported as percent inhibition, in Table 1, below.

TABLE 1

| Example No. | % Inhib. (0.5 nM) |
|---|---|
| Example 1 | 60% |

TABLE 1-continued

| Example No. | % Inhib. (0.5 nM) |
|---|---|
| Example 2 | 66% |
| Example 3 | 64% |
| Example 4 | 67% |
| Example 5 | 69% |
| Example 6 | 60% |
| Example 7 | 73% |
| Example 8 | 54% |
| Example 9 | 65% |
| Example 10 | 70% |
| Example 11 | 62% |
| Example 12 | 61% |
| Example 13 | 66% |
| Example 14 | 63% |
| Example 15 | 45% |
| Example 16 | 49% |
| Example 17 | 50% |
| Example 18 | 82% |
| Example 19 | 51% |
| Example 20 | 37% |
| Example 21 | 44% |
| Example 23 | 51% |
| Example 24 | 40% |
| Example 25 | 45% |
| Example 26 | 42% |
| Example 27 | 50% |
| Example 28 | 77% |
| Example 29 | 64% |
| Example 30 | 55% |
| Example 31 | 48% |
| Example 32 | 66% |

Table 1 shows the inhibitory potencies of compounds of the invention against HIV-1 protease.

Antiviral Activity

The anti-HIV activity of the compounds of the invention can be determined in MT4 cells according to the procedure of Kempf, et. al. (*Antimicrob. Agents Chemother.* 1991, 35, 2209). The $IC_{50}$ is the concentration of compound that gives 50% inhibition of the cytopathic effect of HIV. The $LC_{50}$ is the concentration of compound at which 50% of the cells remain viable.

TABLE 2

| Example No. | $EC_{50}$ (nM) | $LC_{50}$ ($\mu$M) |
|---|---|---|
| Example 1 | 3 | 12.76 |
| Example 2 | 22 | 47.11 |
| Example 3 | 21 | 15.73 |
| Example 4 | 12 | 68.95 |
| Example 5 | 40 | 16.70 |
| Example 6 | 12 | 58.61 |
| Example 7 | 17 | 55.20 |
| Example 8 | 47 | 18.90 |
| Example 9 | 46 | 18.45 |
| Example 10 | 14 | 18.18 |
| Example 11 | 17 | 18.33 |
| Example 12 | 13 | 70.34 |
| Example 13 | 48 | 60.35 |
| Example 14 | 41 | 22.74 |
| Example 15 | 11 | 53.09 |
| Example 16 | 10 | 61.73 |
| Example 17 | 11 | 39.17 |
| Example 18 | 19 | 44.64 |
| Example 19 | 17 | 20.69 |
| Example 20 | 16 | 49.74 |
| Example 21 | 11 | 53.05 |
| Example 23 | 259 | >100 |
| Example 24 | 17 | 55.42 |
| Example 25 | 57 | >100 |
| Example 26 | 817 | 17.35 |
| Example 27 | 374 | 20.60 |

TABLE 2-continued

| Example No. | $EC_{50}$ (nM) | $LC_{50}$ ($\mu$M) |
|---|---|---|
| Example 28 | 11 | 49.52 |
| Example 29 | 175 | 31.15 |
| Example 30 | 20 | 17.87 |
| Example 31 | 58 | 17.22 |
| Example 32 | 15 | 64.14 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include a hydroxyl-substituted compound of formula I or II which has been acylated with a blocked or unblocked amino acid residue, a phosphate function, a hemisuccinate residue, an acyl residue of the formula $R^{14}C(O)$— or $R^{14}C(S)$— wherein $R^{14}$ is hydrogen, lower alkyl, haloalkyl, alkoxy, thioalkoxy, alkoxyalkyl, thioalkoxyalkyl or haloalkoxy, or an acyl residue of the formula $R_a$—$C(R^b)(R^d)$—$C(O)$— or $R_a$—$C(R^b)(R^d)$—$C(S)$— wherein $R^b$ and $R^d$ are independently selected from hydrogen or lower alkyl and $R^a$ is —$N(R^e)(R^f)$, $OR^e$ or —$SR^e$ wherein $R^e$ and $R^f$ are independently selected from hydrogen, lower alkyl and haloalkyl, or an amino-acyl residue having the formula $R^{15}NH(CH_2)_2NHCH_2C(O)$— or $R^{15}NH(CH_2)_2OCH_2C(O)$— wherein $R^{15}$ is hydrogen, lower alkyl, arylalkyl, cycloalkylalkyl, alkanoyl, benzoyl or an α-amino acyl group. The amino acid esters of particular interest are glycine and lysine; however, other amino acid residues can also be used, including those wherein the amino acyl group is —$C(O)CH_2NR^{16}R^{17}$ wherein $R^{16}$ and $R^{17}$ are independently selected from hydrogen and lower alkyl, or the group —$NR^{16}R^{17}$, where $R^{16}R^{17}$, taken together, forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. Other prodrugs include a hydroxyl-substituted compound of formula I or II wherein the hydroxyl group is functionalized with a substituent of the formula —CH($R^{18}$)OC(O)$R^{19}$ or —CH($R^{18}$)OC(S)$R^{19}$ wherein $R^{19}$ is lower alkyl, haloalkyl, alkoxy, thioalkoxy or haloalkoxy and $R^{18}$ is hydrogen, lower alkyl, haloalkyl, alkoxycarbonyl, aminocarbonyl, alkylaminocarbonyl or dialkylaminocarbonyl. Such prodrugs can be prepared according to the procedure of Schreiber (Tetrahedron Lett. 1983, 24, 2363) by ozonolysis of the corresponding methallyl ether in methanol followed by treatment with acetic anhydride.

The prodrugs of this invention are metabolized in vivo to provide the hydroxyl-substituted compound of formula I or II. The preparation of the prodrug esters is carried out by reacting a hydroxyl-substituted compound of formula I or II with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (halo)alkyl esters, transacetalization with bis(alkanoyl)acetals or condensation of the hydroxyl group with an activated aldehyde followed by acylation of the intermediate hemiacetal.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, dideoxycytidine (DDC), dideoxyinosine (DDI), BCH-189, AzdU, carbovir, DDA, D4C, D4T, DP-AZT, FLT (fluorothymidine), BCH-189,5-halo-3'-thiadideoxycytidine, PMEA, zidovudine (AZT) and the like), non-nucleoside reverse transcriptase inhibitors (for example, R82193, L-697,661, BI-RG-587 (nevirapine), DMP-266, and the like) retroviral protease inhibitors (for example, HIV protease inhibitors such as ritonavir, ABT-378, saquinavir, nelfinavir, indinavir, VX-478 (amprenavir), SC-52151, KNI-227, KNI-272, U-140690, DMP-450, and the like), HEPT compounds, L,697,639, R82150, U-87201 E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-IgG, CD4-PE40, butyl-DNJ, hypericin, oxamyristic acid, dextran sulfate and pentosan polysulfate. Immunomodulators that can be administered in combination with a compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis facator, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, FK-565, FK-506, G-CSF, GM-CSF, hyperthermia, isopinosine, IVIG, HIVIG, passive immunotherapy and polio vaccine hyperimmunization. Other anti-infective agents that can be administered in combination with a compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-lmmunogen, p24 (recombinant), VaxSyn HIV-1 (p24) can be used in combination with a compound of the present invention.

Other agents that can be used in combination with the compounds of this invention are ansamycin LM 427, apurinic acid, ABPP, Al-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofyl]ine, pentoxifyl]ine, Peptide T, pine cone extract, polymannoacetate, reticulose, retrogen, ribavirin, ribozymes, RS-47,Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compounds of this invention are antifungals such as amphotericin B, clotrimazole, flucytosine, fluconazole, itraconazole, ketoconazole and nystatin and the like.

Other agents that can be used in combination with the compounds of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compounds of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compounds of this invention are drugs for treating neurological disease such as peptide T, ritalin, lithium, elavil, phenytoin, carbamazipine, mexitetine, heparin and cytosine arabinoside and the like.

Other agents that can be used in combination with the compounds of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for treatment of HIV or AIDS in combination with the compounds of this invention are reverse transcriptase inhibitors and other HIV protease inhibitors.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound having formula I:

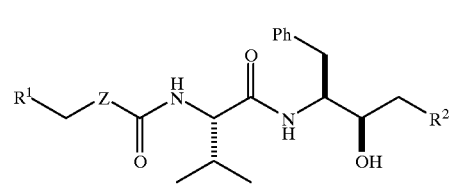

wherein $R^1$ is a thiazolyl group having the formula

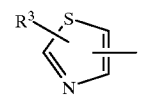

and $R^2$ is a group having the formula:

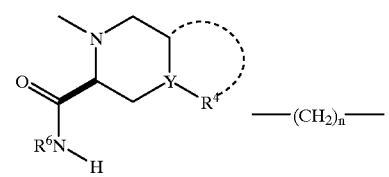

wherein $R^3$ is selected from the group consisting of hydrogen, alkyl, amino, alkylamino, dialkylamino and cycloalkyl; and Y is N;

R⁴ is —W—R⁵;
W is —(CH₂)ₙ—; and R⁵ is selected from the group consisting of alkyl, and aryl; n is from 0 to 6; or R⁴ and the ring taken together can form a bicyclic group having the formula:

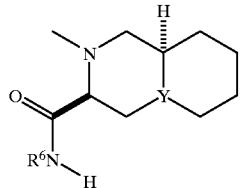

with the proviso that when W is O, or S then Y is CH;
R⁶ is hydrogen, alkyl, cycloalkyl, aryl, (aryl)alkyl, heterocyclic, (heterocyclic)alkyl, heteroaryl, or (heteroaryl)alkyl; and
Z is —O—, —S—, —CH₂— or —N(R⁷)—; and R⁷ is hydrogen, alkyl, aryl, (aryl)alkyl, heterocyclic, (heterocyclic)alkyl, heteroaryl, or (heteroaryl)alkyl;
wherein the alkyl, aryl, heterocyclic, and heteroaryl groups can be optionally substituted with 1 to 5 substituents selected from the group consisting of hydroxy, alkoxy, amino, alkylamino, dialkylamino and halogen;
or a pharmaceutically acceptable salt, ester or prodrug thereof.

2. The compound according to claim 1, wherein R³ is alkyl or cycloalkyl and Z is —O—, or —N(R⁷)—.

3. The compound according to claim 2, wherein R³ is alkyl.

4. The compound according to claim 2, wherein R³ is cycloalkyl selected from the group consisting of cyclopropyl, cyclobutyl, cyclopentyl, and cyclohexyl.

5. The compound according to claim 3, wherein R³ is selected from the group consisting of hydrogen, methyl, ethyl, propyl and isopropyl.

6. The compound according to claim 5, wherein R³ is isopropyl.

7. The compound according to claim 1, wherein Z is —O—.

8. The compound according to claim 1, wherein Z is —N(R⁷)— and R⁷ is methyl.

9. The compound according to claim 1, wherein Y is nitrogen, W is —CH₂— and R⁵ is aryl selected from the group consisting of phenyl, methylenedioxyphenyl, and heteroaryl.

10. The compound according to claim 9, wherein R⁵ is substituted with fluorine.

11. The compound according to claim 9, wherein R⁵ is substituted with 1 to 3 hydroxy groups.

12. The compound according to claim 9, wherein R⁵ is substituted with 1 to 3 alkoxy or alkylthio groups.

13. The compound according to claim 9, wherein R⁵ is substituted with two alkoxy groups.

14. The compound according to claim 9, wherein R⁵ is substituted with at least one hydroxy group and at least one methoxy group.

15. The compound according to claim 1, wherein R⁶ is selected from the group consisting of alkyl, hydroxyalkyl, and cycloalkyl.

16. The compound according to claim 15, wherein R⁶ is lower alkyl selected from the group consisting of methyl, ethyl, propyl, or butyl.

17. The compound according to claim 16, wherein R⁶ is tert-butyl or hydroxybutyl.

18. A compound selected from the group consisting of:
2-(1-methylethyl)-4-thiazolylmethyl-((1S)-1-((((1S,2R)-3-((2S)-4-(1,3-benzodioxol-5-ylmethyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-(phenylmethyl)-1-piperazinyl)-2-hydroxy-1-(phenylmethyl)propyl)amino)carbonyl)-2-methylpropyl)carbamate;

2-(1-methylethyl)-4-thiazolylmethyl-(1S)-1-((((1S,2R)-3-((2S)-2-(((1,1-dimethylethyl)amino)carbonyl)-4-((4-fluorophenyl)methyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-(5-thienylmethyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-(4-(3-hydroxyphenyl)methyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-(3-pyridinylmethyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-(4-pyridinylmethyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-((4-hydroxyphenyl)methyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-4-(1H-benzimidiazol-2-ylmethyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-2-(((1,1-dimethylethyl)amino)carbonyl)-4-(2-quinolinylmethyl)-1-piperazinyl)-2-hydroxy-1-(phenylmethyl)propyl)amino)carbonyl)-2-methylpropyl)carbamate;

2-(1-methylethyl)-4-thiazolylmethyl-((1S)-1-((((1S,2R)-3-((2S)-4-((3,4-dimethoxylphenyl)methyl)-2-(((1,1-dimethylethyl)amino)carbonyl)-1-piperazinyl)-2-hydroxy-1-(phenylmethyl)propyl)amino)carbonyl)-2-methylpropyl)carbamate;

N'-((1S)-1-((((1S,2R)-3-((2S)-2-(((1,1-dimethylethyl)amino)carbonyl)-4-(5-thiazolylmethyl)-1-piperazinyl)-2-hydroxy-1-(phenylmethyl)propyl)amino)carbonyl)-2-methylpropyl)-N-methyl-N-(2-(1-methylethyl)-4-thiazolylmethyl)urea;

N'-((1S)-1-((((1S,2R)-3-((2S)-2-(((1,1-dimethylethyl)amino)carbonyl)-4-(phenylmethyl)-1-piperazinyl)-2-hydroxy-1-(phenylmethyl)propyl)amino)carbonyl)-2-methylpropyl)-N-methyl-N-(2-(1-methylethyl)-4-thiazolylmethyl)urea;

N'-((1S)-1-((((1S,2R)-3-((2S)-2-(((1,1-dimethylethyl)amino)carbonyl)-4-((4-hydroxy-3-methoxyphenyl)methyl)-1-piperazinyl)-2-hydroxy-1-(phenylmethyl)propyl)amino)carbonyl)-2-methylpropyl)-N-methyl-N-(2-(1-methylethyl)-4-thiazolylmethyl)urea;

2-methyl-4-thiazolylmethyl-((1S)-1-((((1S,2R)-3-((2S)-4-(1,3-benzodioxol-5-ylmethyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-methyl-4-thiazolylmethyl-((1S)-1-((((1S,2R)-3-((2S)-4-((3,4-dimethoxyl-phenyl)methyl)-2-(((1,1-dimethylethyl)amino)carbonyl)-1-piperazinyl)-2-hydroxy- 1-(phenylmethyl)propyl)amino)carbonyl)-2-methylpropyl)carbamate;

2-methyl-4-thiazolylmethyl-((1S)-1-((((1S,2R)-3-((2S)-2-(((1,1-dimethyl-ethyl)amino)carbonyl)-4-((4-fluorophenyl)methyl)-1-piperazinyl)-2-hydroxy-1-(phenylmethyl)propyl)amino)carbonyl)-2-methylpropyl)carbamate;

2-ethyl-4-thiazolylmethyl-(1S)-1-((((1S,2R)-3-((2S)-4-((3,4-dimethoxylphenyl)methyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-(1-methylethyl)-5-thiazolylmethyl-((1S)-1-((((1S,2R)-3-((2S)-4-((3,4-dimethoxylphenyl)methyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-ethyl-5-thiazolylmethyl-(1S)-1-((((1S,2R)-3-((2S)-4-((3,4-dimethoxylphenyl)methyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-methyl-5-thiazolylmethyl-((1S)-1-((((1S,2R)-3-((2S)-4-((3,4-dimethoxyl-phenyl)methyl)-2-(((1,1-dimethylethyl)amino)carbonyl)-1-piperazinyl)-2-hydroxy-1-(phenylmethyl)propyl)amino)carbonyl)-2-methylpropyl)carbamate;

N'-((1R)-1-((((1S,2R)-3-((2S)-2-(((1,1-dimethylethyl)amino)carbonyl)-4-(5-thiazolylmethyl)-1-piperazinyl)-2-hydroxy-1-(phenylmethyl)propyl)amino)carbonyl)-2-methylpropyl)-N-methyl-N-(5-thiazolylmethyl)urea;

N'-((1S)-1-((((1S,2R)-3-((2S)-2-(((1,1-dimethylethyl)amino)carbonyl)-4-(5-thiazolylmethyl)-1-piperazinyl)-2-hydroxy-1-(phenylmethyl)propyl)amino)carbonyl)-2-methylpropyl)-N-methyl-N-(5-thiazolylmethyl)urea;

5-thiazolylmethyl-((1S)-1-((((1S,2R)-3-((2S)-2-(((1,1-dimethylethyl)amino)carbonyl)-4-(phenylmethyl)-1-piperazinyl)-2-hydroxy-1-(phenylmethyl)propyl)amino)carbonyl)-2-methylpropyl)carbamate;

5-thiazolylmethyl-(1S)-1-((((1S,2R)-3-((2S)-2-(((1,1-dimethylethyl)amino)carbonyl)-4-(5-thiazolylmethyl)-1-piperazinyl)-2-hydroxy-1-(phenylmethyl)propyl)amino)carbonyl)-2-methylpropyl)carbamate;

S-(2-(1-methylethyl)-4-thiazolylmethyl)((1S)-1-((((1S,2R)-3-((2S)-4-(1,3-benzodioxol-5-ylmethyl)-2-(((1,1-dimethylethyl)amino)carbonyl)-1-piperazinyl)-2-hydroxy-1-(phenylmethyl)propyl)amino)carbonyl)-2-methylpropyl)-carbamothioate; and 4-(1,3-benzodioxol-5-ylmethyl)-N-(1,1-dimethylethyl)-1-((2R,3)-3-(((2S)-2-((3-(2-(1-methylethyl)-4-thiazolyl)-1-oxopropyl)amino)-3-methyl-1-oxo-butyl)amino)-2-hydroxy-4-phenylbutyl)-2-piperazinecarboxamide;

or a pharmaceutically acceptable salt, ester or prodrug thereof.

19. The compound according to claim 18, selected from the group consisting of:

2-(1-Methylethyl)-4-thiazolylmethyl-((1S)-1-((((1S,2R)-3-((2S)-4-(1,3-benzodioxol-5-ylmethyl)-2-(((1,1-dimethylethyl)amino)carbonyl)-1-piperazinyl)-2-hydroxy-1-(phenylmethyl)propyl)amino)carbonyl)-2-methylpropyl)carbamate;

2-(1-Methylethyl)-4-thiazolylmethyl-((1S)-1-((((1S,2R)-3-((2)-2-(((1,1-dimethylethyl)amino)carbonyl)-4-(5-thienylmethyl)-1-piperazinyl)-2-hydroxy-1-(phenylmethyl)propyl)amino)carbonyl)-2-methylpropyl)carbamate; and 2-(1-Methylethyl)-4-thiazolylmethyl-((1S)-1-((((1S,2R)-3-((2S)-4-((3,4-dimethoxylphenyl)methyl)-2-(((1,1-dimethylethyl)amino)carbonyl)-3-piperazinyl)-2-hydroxy-1-(phenylmethyl)propyl)amino)carbonyl)-2-methylpropyl)carbamate or a pharmaceutically acceptable salt, ester or prodrug thereof.

20. A pharmaceutical composition for treating an HIV infection comprising a pharmaceutical carrier and a therapeutically effective amount of a compound of claim 1.

21. A pharmaceutical composition for treating an HIV infection comprising a pharmaceutical carrier and a therapeutically effective amount of a compound of claim 9.

22. A pharmaceutical composition for treating an HIV infection comprising a pharmaceutical carrier and a therapeutically effective amount of a compound of claim 18.

23. A pharmaceutical composition for treating an HIV infection comprising a pharmaceutical carrier and a therapeutically effective amount of a compound of claim 19.

24. A method for inhibiting HIV protease comprising administering to a mammal in need of such treatment a therapeutically effective amount of a compound of claim 1.

25. A method for treating an HIV infection comprising administering to a human in need of such treatment a therapeutically effective amount of a compound of claim 1.

26. A method for treating an HIV infection comprising administering to a human in need of such treatment a therapeutically effective amount of a compound of claim 18.

27. A method for inhibiting HIV protease comprising administering to a human in need of such treatment a therapeutically effective amount of a compound of claim 18.

28. A method for treating an HIV infection comprising administering to a human in need of such treatment a therapeutically effective amount of a compound of claim 19.

29. A method for inhibiting HIV protease comprising administering to a human in need of such treatment a therapeutically effective amount of a compound of claim 19.

30. A process for the preparation of a compound of the formula I:

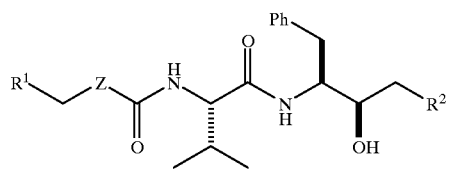

I wherein R¹ is a thiazolyl group having the formula

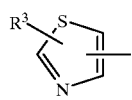

and R² is a group having the formula:

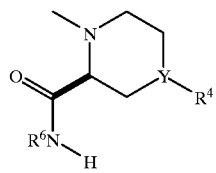

wherein R³ is selected from the group consisting of hydrogen, alkyl, amino, alkylamino, dialkylamino and cycloalkyl; and Y is CH or N;

R⁴ is —W—R⁵;

W is —O—, —S—, or —(CH$_2$)$_n$—; and R⁵ is selected from the group consisting of alkyl, and aryl; n is from 0 to 6; or R⁴ and the ring taken together can form a bicyclic group having the formula:

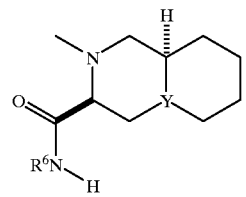

with the proviso that when W is O, or S then Y is CH;

R⁶ is hydrogen, alkyl, cycloalkyl, aryl, (aryl)alkyl, heterocyclic, (heterocyclic)alkyl, (heterocyclic)alkyl, heteroaryl, or (heteroaryl)alkyl; and Z is —O—, —S—, —CH$_2$— or —N(R⁷)—; and R⁷ is hydrogen, alkyl, aryl, (aryl)alkyl, heterocyclic, heteroaryl, or (heteroaryl)alkyl;

wherein the alkyl, aryl, heterocyclic, and heteroaryl groups can be optionally substituted with 1 to 5 substituents selected from the group consisting of hydroxy, alkoxy, alkylthio, amino, alkylamino, dialkylamino and halogen.

\* \* \* \* \*